United States Patent [19]

Cooper et al.

[11] Patent Number: 4,780,562
[45] Date of Patent: Oct. 25, 1988

[54] PROCESSES AND INTERMEDIATES FOR MAKING 16-PHENOXY AND 16-SUBSTITUTED PHENOXY-PROSTATRIENOIC ACID DERIVATIVES AND THEIR STEREOISOMERS

[75] Inventors: Gary F. Cooper, Portola Valley; Douglas L. Wren, Palo Alto; Albert R. Van Horn, San Jose; Tsung-Tee Li, Los Altos Hills; Colin C. Beard, Palo Alto, all of Calif.

[73] Assignee: Syntex (U.S.A.) Inc., Palo Alto, Calif.

[21] Appl. No.: 776,063

[22] Filed: Sep. 13, 1985

Related U.S. Application Data

[63] Continuation-in-part of Ser. No. 564,386, Dec. 22, 1983.

[30] Foreign Application Priority Data

Dec. 18, 1984 [PK] Pakistan .................. S19/84

[51] Int. Cl.$^4$ ............................................. C07C 17/00
[52] U.S. Cl. ......................................... 560/53; 560/121
[58] Field of Search ................................ 560/121, 53

[56] References Cited

U.S. PATENT DOCUMENTS 4,578,505  3/1986  Collins ................. 560/121

*Primary Examiner*—Paul J. Killos
*Attorney, Agent, or Firm*—Derek P. Freyberg

[57] ABSTRACT

This invention relates to a process for making a compound of formula I

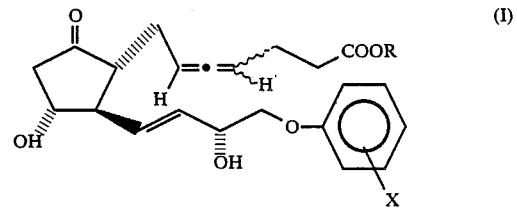

in the form of a stereoisomer or mixture thereof, wherein R is hydrogen, lower alkyl; X is hydrogen, halo, trifluoromethyl, lower alkyl or lower alkoxy, and the wavy lines represent the α or β configuration with the proviso that when one wavy line is α the other is β, or a pharmaceutically acceptable, non-toxic salt of the compound wherein R is hydrogen; novel intermediates useful for preparing these compounds; processes for making the intermediates; and a stereoisomer of the compound of formula I wherein R is methyl and X is hydrogen and a process for making same.

57 Claims, No Drawings

PROCESSES AND INTERMEDIATES FOR MAKING 16-PHENOXY AND 16-SUBSTITUTED PHENOXY-PROSTATRIENOIC ACID DERIVATIVES AND THEIR STEREOISOMERS

RELATED APPLICATIONS

This application is a continuation-in-part of U.S. patent application Ser. No. 564,386, filed Dec. 22, 1983, now allowed, which is hereby incorporated in full by reference.

BACKGROUND OF THE INVENTION

The present invention relates to a process for making compounds in the form of a stereoisomer or mixture thereof, of 16-phenoxy and 16-(o, m or p)-substituted phenoxy prostaglandin derivatives represented by the following formula

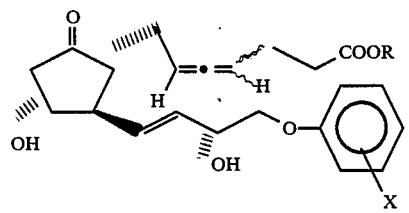

(I)

wherein R is hydrogen, lower alkyl; X is hydrogen, halo, trifluoromethyl, lower alkyl or lower alkoxy, and the wavy lines represent the α or β configuration with the proviso that when one wavy line is α the other is β, or a pharmaceutically acceptable, non-toxic salt of the compound wherein R is hydrogen; certain novel intermediates for making these compounds and a stereoisomer of the compound of formula I wherein R is methyl and X is hydrogen and a process for preparing same.

The compounds of formula I are disclosed in U.S. Pat. No. 4,178,457.

The synthesis described herein addresses the twin problems of how to prepare an individual stereoisomer of the subject compounds while allowing selective deprotection of the C-9 hydroxyl group so it can be oxidized without also oxidizing the C-11 and C-15 groups and that the subsequent deprotection of C-11 and C-15 will not degrade the resulting molecule.

The problem of preparing an individual stereoisomer is solved by going through a novel propargyl alcohol intermediate which, though it is made as a diastereomeric mixture, can be separated into its two stereochemically pure isomers. One isomer of this stereochemically pure propargyl alcohol is then converted to a single, stereochemically pure allenic compound by employing a stereospecific homologation/rearrangement reaction in the next step. Starting with a specific stereochemically pure phenoxy lactone compound, which is available in the art, one can open the lactone and convert the resulting acid to an aldehyde. This novel aldehyde is reacted with a metal acetylide to give a propargyl alcohol having two stereoisomers. The two isomers can be separated into two stereochemically pure fractions by chromatographic means where one has properly selected one ether-forming protecting groups at C-9, C-11 and C-15, particularly at C-9. It has been found that a bulky ether-forming group at C-9 is necessary to effect readily this separation. For example, when the C-9 hydroxyl protecting group is an appropriate alkyl, aryl or arylalkyl substituted silyl ether, separation of the two propargyl alcohol isomers may be readily effected where otherwise separation is usually difficult and incomplete. The second essential step is to convert one stereochemically pure isomer to a single stereochemically pure allene-containing compound. This is accomplished by a hologation/rearrangement reaction using a trialkyl orthoacetate reagent and temperature.

The other problem is to design a synthetic sequence which will allow selective deprotection of the C-9 hydroxyl group so it can be oxidized, and then removal of the C-11 and C-15 hydroxyl protection groups without decomposing the resulting molecule. This is accomplished here by protecting C-9 with a base-labile ether-forming group while protecting C-11 and C-15 with base-stabile ether-forming groups. Then it is possible to drop off the C-9 protecting group, oxidize the hydroxyl group and then deprotect C-11 and C-15 under mild acid conditions. This sequence is essential because base would cause elimination-rearrangement to the "B" type prostaglandin and catalytic hydrogenation would affect the allene group.

The described process also provides an efficient method of preparing the compounds of U.S. Pat. No. 4,178,457, in particular in the form of mixtures of the four components which are included in formula I as defined below.

The compounds of U.S. Pat. No. 4,178,457 are known to be useful in the treatment of mammals where prostaglandins are indicated. They are particularly useful as inhibitors of gastric secretion. It has also been found that the stereoisomer of the compound of formula I possessing the R allene configuration wherein R is methyl and X is hydrogen having the following structure

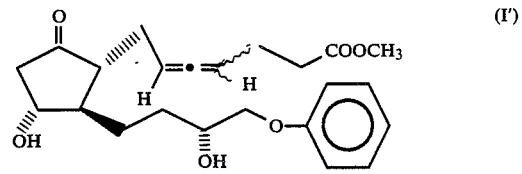

(I')

has excellent biological properties (for example potency, low toxicity etc.) and other properties which affect its pharmaceutical use (for example chemical stability, shelf life etc.). A study conducted in rats showed that the antisecretory ED$_{50}$ for this individual R allenic stereoisomer is about 6 μg/Kg.

Furthermore, this R allenic stereoisomer occurs in crystalline form.

Prostaglandins often are oily materials. The racemic diastereoisomeric mixture of the compounds of formula I wherein R is methyl and X is hydrogen is known to be a viscous oil (see U.S. Pat. No. 4,178,457) or low melting waxy solid. The compound which is structurally closest to the R allene stereoisomer of formula I' and its racemic diastereoisiomeric mixture, namely (dl) 9α,1-1α,15α-trihydroxy-16-phenoxy-17,18,19,20-tetranor-prosta-4,5,13(E)-trienoic acid methyl ester (a compound in Example 16 of U.S. Pat. No. 3,985,791) also occurs as an oil. The R allenic stereoisomer of formula I' was first obtained as an oil, but when stored in the freezer to be stabilized, surprisingly, the oily material spontaneously crystallized. The crystallized material has a melting point above 70° C. In contrast with this isomer, the corresponding racemic diastereoisiomeric mixture, when stored in the freezer under the same conditions, takes about 1-3 weeks to become waxy solid. The S allene stereoisomer corresponding to formula I' never crystallized under similar conditions.

In addition, it was reported in UK Pat. No. 1,288,174, U.S. Pat. No. 4,005,133 and EPO Publication No. 97,439 that in order to have free-flowing crystalline solid materials, prostaglandins had to be converted into their organic or inorganic salts. Therefore, it is also surprising that the R allenic stereoisomer of formula I', without being converted into a salt, is a free-flowing crystalline material.

The crystalline material of formula I' can be easily purified using conventional techniques. The crystallinity of this material facilitates handling and chemical analysis and improves chemical stability. Furthermore, the crystalline material of formula I' can be readily formulated into solid dosage forms.

DEFINITIONS

Formulas having an allene group are represented herein as having substituents on one end of the allene group which are oriented at 90° to those on the other. A broken line indicates that the substituent is behind the plane of the allene group and is designated as being in the α configuration. A triangular line defines the substituent as being in front or the plane of the allene group and is referred to as being in the β configuration. When there are at least three different groups substituted on the allene, as in formula I, the allene moiety is rendered asymmetric.

The broken lines shown in the above formula and other formulas herein at carbons 8, 9, 11 and 15 indicate that the pendent substituents are in the α configuration, i.e., below the plane of the cyclopentane ring or of the lower side chain. The triangular shaped line at C-12 denotes the β configuration, i.e. that the substituent is above the plane of the cyclopentane ring.

The double bond at C-13 in these formulas has the trans configuration, the same as do the natural PGE and PGF series prostaglandins.

The compounds of this invention possess asymmetric centers and thus can be produced as racemic or non-racemic mixtures or as individual R- or S-enantiomers. The individual enantiomers may be obtained by resolving a racemic or non-racemic mixture of an intermediate at some appropriate stage of the synthesis. It is understood that the racemic or non-racemic mixtures and the individual R- or S-enantiomers are encompassed within the scope of the present invention.

Formula I includes any single structure below (Ia, Ia', Ib and Ib'), all permutations of two or three components in any proportions, and mixtures of all four components in any proportions.

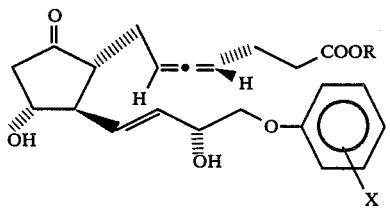
(Ia)

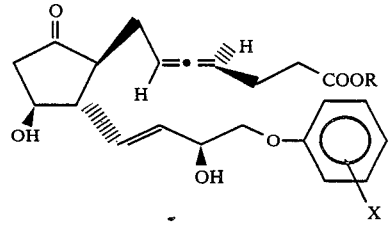
(Ia')

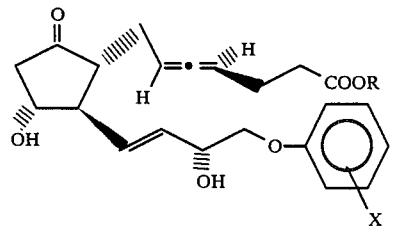
(Ib)

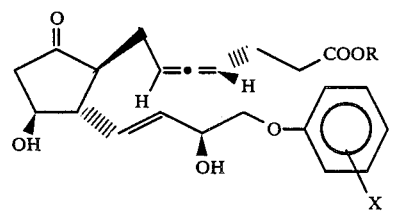
(Ib')

Any individual component may be prepared by processes described below starting from the appropriate individual enantiomers of the lactone of formula 1 in the reaction scheme on page 11. Mixtures of Ia and Ia', Ib and Ib', Ia and Ib, Ia' and Ib' and mixtures of the four components may also be prepared by processes described below. Mixtures of Ia and Ia' or Ib and Ib' or mixtures of all four components are produced starting from the racemic or non-racemic modifications of the lactone of formula 1. Mixtures of Ia and Ib, or Ia' and Ib' are prepared starting from the appropriate optically active lactone of formula 1. All the mixtures above the mixtures of Ia and Ib' and Ib and Ia' may also be prepared by mixing the appropriate intermediates or individual components obtained by the processes described below. Any mixtures of three components may be prepared by mixing the appropriate intermediates or individual components obtained by the processes described below.

For the sake of simplicity only one enantiomer, i.e., the enantiomer having the natural prostaglandin configuration will be depicted in the description of the process; however, it is to be understood that the racemic and non-racemic mixtures and the individual unnatural enantiomers are also encompassed thereby, they being obtained by starting with the corresponding racemic or non-racemic mixture or unnatural enantiomer.

The natural configurations are represented by the formula Ia and Ib. The unnatural configurations are represented by the formula Ia' and Ib'.

The term "mixture", as applied to formula I is defined in the present application as any combination of all four components (of formula Ia, Ia' Ib and Ib' as depicted above) in any proportions and all permutations of any two or three of the four components in any proportions. As applied to synthetic intermediates of formulas II–VIII in the claims (or formulas 8–17 in the reaction scheme on pages 11–12), the term "mixture" is defined in the present application as any combination of the stereoisomers implied by the wavy lines and the enantiomers of such stereoisomers in any proportions.

The use of the symbol "R" preceding a substituent designates the absolute stereochemistry of that substituent according to the Cahn-Ingold-Prelog rules [see Cahn et al., Angew. Chem. Inter. Edit., Vol. 5, p. 385 (1966), errata p. 511; Cahn et al., Angew. Chem., Vol. 78, p. 413 (1966); Cahn and Ingold, J. Chem. Soc., (London), 1951, p. 612; Cahn et al., Experientia, Vol. 12, p. 81 (1956); Cahn J. Chem. Educ., Vol. 41, p. 116 (1964)]. Because of the interrelation of the designated substituent with the other substituents in a compound having $\alpha$ or $\beta$ prefixes, the designation of the absolute configuration of one substituent fixes the absolute configuration of all substituents in the compound and thus the absolute configuration of the compound as a whole.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other.

"Diastereoisomers" are stereoisomers which are not mirror-images of each other.

"Epimers" are diastereomers which differ only in the configuration of one asymmetric center.

"Racemic mixture" means a mixture containing equal parts of individual enantiomers. "Non-racemic mixture" is a mixture containing unequal parts of individual enantiomers.

For the purpose of this invention, the terms "lower alkyl" or "alkyl" mean a straight or branched alkyl radical of 1 to 6 carbon atoms. Examples of such radicals are methyl, ethyl, propyl, isopropyl, butyl, t-butyl, i-butyl, sec-butyl, pentyl, hexyl and the like. Lower alkoxy means an —OR radical wherein R is lower alkyl. Halo refers to fluoro, chloro, bromo and iodo. Aryl refers to aryl groups wherein the ring system contains 6-10 carbon atoms not counting substituents, such as phenyl, naphthyl or the like. Lower alkyl aryl refers to an aryl group as defined above having a lower alkyl chain wherein lower alkyl is defined above. Substituted lower alkyl aryl refers to a radical wherein the aryl group defined above of a lower alkyl aryl defined above is substituted with one or more lower alkyl, halo, or lower alkoxy radicals as these latter terms are defined above.

The term "w/v%" (percent weight in volume) indicates the number of g of a constituent in 100 ml of solution.

The term "pharmaceutically acceptable, non-toxic salts" refers to those base-derived salts of any compound herein having a carboxylic acid function. These salts are derived from pharmaceutically acceptable, non-toxic inorganic or organic bases.

Salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic, non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, dicyclohexylamine, lysine, arginine, histidine, caffeine, procaine, hydrabamine, choline, betaine, ethylenediamine, glucosamine, N-methylglucamine, theobromine, purines, piperazine, piperidine, N-ethylpiperidine, polyamine resins and the like. Particularly preferred organic non-toxic bases are isopropylamine, diethylamine, ethanolamine, tromethamine, dicyclohexylamine, choline and caffeine.

The acid salts of these compounds, where appropriate to make, are prepared by treating the corresponding free acids of the compounds with at least one molar equivalent of a pharmaceutically acceptable base. Representative pharmaceutically acceptable bases are sodium hydroxide, potassium hydroxide, ammonium hydroxide, calcium hydroxide, trimethylamine, lysine, caffeine, and the like. The reaction is conducted in water, alone or in combination with an inert, water-miscible organic solvent, at a temperature of from about 0° C. to about 100° C., preferably at room temperature. Typical inert, water-miscible organic solvents include methanol, ethanol, or dioxane. The molar ratio of compounds of formula I to base used are chosen to provide the ratio desired for any particular salt.

The numbering of these compounds follows that in use for the naturally occuring PGE and PGF compounds, illustrated as follows:

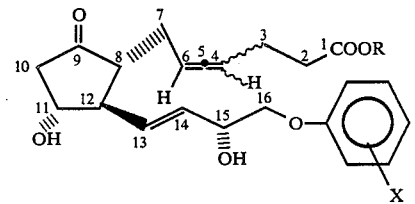

For analytical purposes, in this disclosure a carbon of a particular intermediate is identified by the number it will have in the final product, ie formula I. Thus, for example, in formula 8 in the Reaction Scheme below, the carbon on which the $R^2$ ether group is substituted is designated C-9 as that is the numbering of that carbon in formula I.

The process for preparing the instant compounds, including the novel intermediates is outlined in the following reaction scheme.

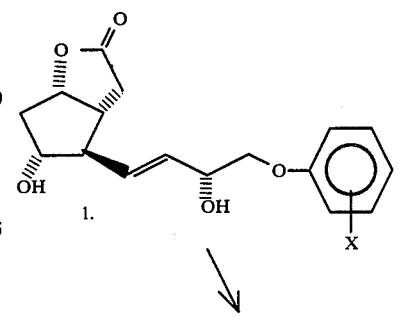

1.

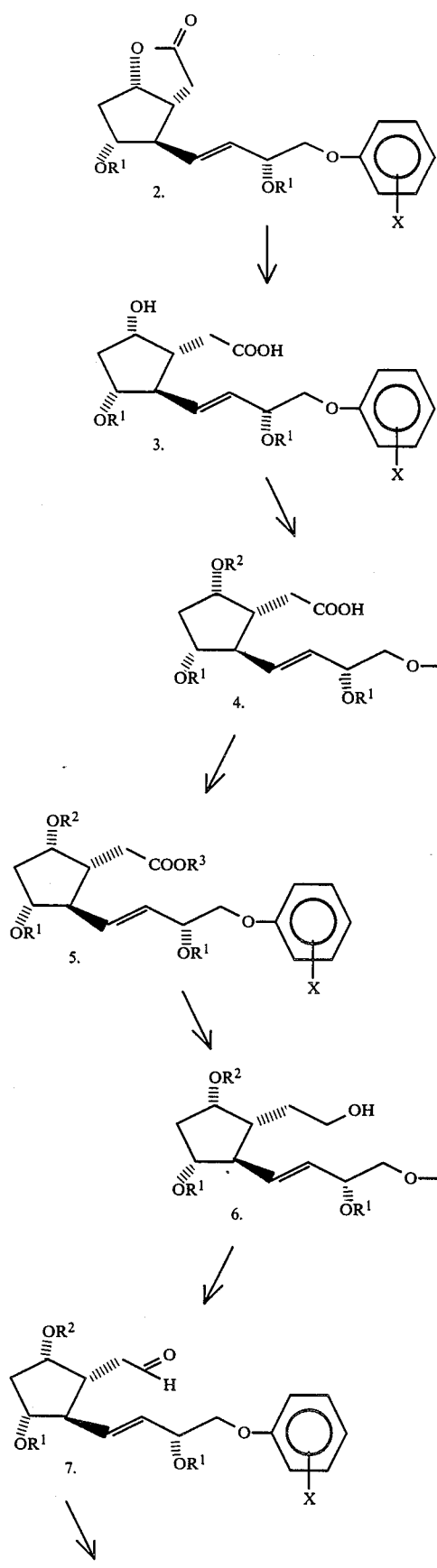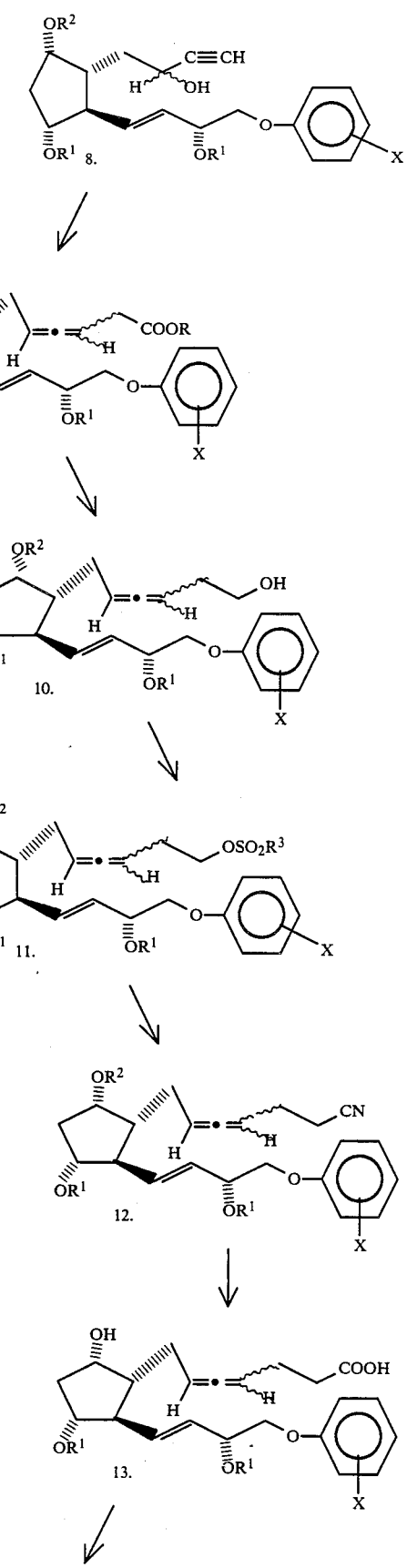

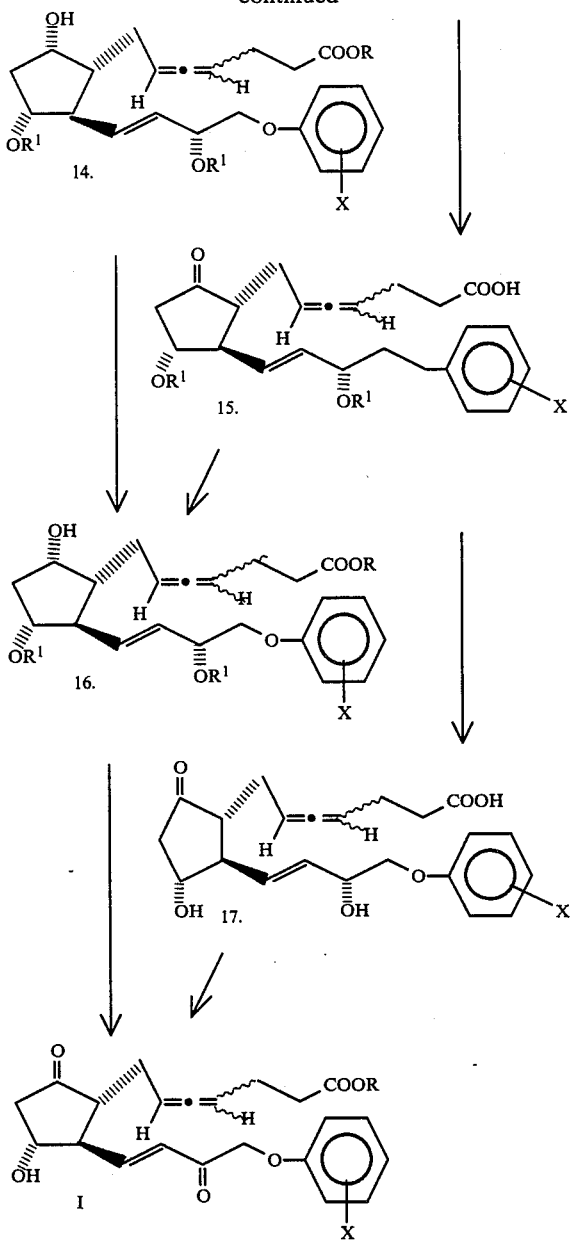

In the preceding flow sheet $R^1$ is a base-stabile, acid-labile ether-forming group as defined below, $R^2$ is a base-labile ether-forming radical as defined below and M is hydrogen or a metal ion such as an alkali metal ion.

DETAILED DESCRIPTION OF THE PROCESS

The starting material, formula 1, can be prepared according to the procedures set forth in U.S. Pat. Nos. 3,880,712, 3,985,791, and 4,304,907, which procedures are incorporated herein by reference and made a part hereof.

Before opening the lactone ring of formula 1, the two hydroxyl groups are converted to ethers. These two groups are designated $R^1$ and defined as base-stabile, acid-labile ether-forming groups. Such a group may be any ether-forming group which will not be hydrolyzed when treated with a strong aqueous base such as sodium or potassium hydroxide, yet will be hydrolyzed by acid under mild conditions, conditions which will not not result in degradation of the product, formula I. Examples of groups which are base-stabile yet acid-labile are tetrahydrofuranyl, tetrahyropyranyl, 2-ethoxyethyl and the like. Excluded from this definition are alkyl ethers, benzyl ether and alkylaryl ethers, and the like. The conditions normally required to effect acid hydrolysis of these latter ethers would cause product degradation during the hydrolysis process, if in fact their hydrolysis would be effected by acid at all.

It is preferred to protect the C-11 and C-15 hydroxyl groups with tetrahydropyranyl, tetrahydrofuranyl or 2-ethoxyethyl. Ether formation with any of these groups is generally carried out in an aprotic solvent such as a halogenated hydrocarbon with an acid catalyst using amounts and conditions well known in the art. Preferably the acid catalyst is employed in amounts up to 5% by weight of the reactants. Most preferably, the ether-forming reagent will be dihydropyran, at least about 2.1 equivalents, the reaction being carried out in methylene chloride in the presence of p-toluenesulfonic acid. The reaction is generally carried out at between 20°–50° C., preferably at ambient temperature over a period of 15 minutes to four hours preferably about two hours.

Hydrolytic cleavage of the lactone ring is effected by means of a base, preferably an aqueous alkali metal base in a polar organic solvent. An aqueous solution of base such as lithium hydroxide, sodium hydroxide, potassium hydroxide, or the like, is added to a polar organic solvent containing the lactone, all under an inert atmosphere, e.g. nitrogen. The concentration of the added base preferably will be about 1–4M, more preferably between 2.8–3M. A slight molar excess of base is used, preferable 1.05 moles per mole of lactone. Potassium hydroxide is the preferred base. The aqueous base solution is added under nitrogen to a premade solution of the lactone in a solvent such as tetrahydrofuran or a simple alcohol such as methanol. The hydrolysis is effected between room temperature and 100° C., preferably by heating the solution at reflux under nitrogen. It is advantageous to monitor the reaction's progress by thin layer chromatography (tlc).

The hydroxyl group generated by hydrolysis of the lactone is converted to an ether using a reagent which will give a base-labile ether. This group is designated $R^2$ and is defined as a base-labile ether-forming group. This group is best exemplified by $-SiR_4R_5R_6$ where $R_4$, $R_5$ and $R_6$ are alkyl, phenyl or arylalkyl except that all three may not be simultaneously methyl. For the purpose of this invention, alkyl means a radical of 1 to 6 carbon atoms. Arylalkyl is a radical wherein alkyl has the same meaning as lower alkyl and aryl is exemplified by but not limited to phenyl, alkyl substituted phenyl, and naphthyl. Particularly preferred silyl groups are t-butyldimethylsilyl, triisopropylsilyl, triphenylsilyl, t-butyldiphenylsilyl and 2,4,6-tri-t-butylphenoxydimethylsilyl radicals.

When a silylating agent is employed, standard conditions normally used for such a reagent are used. For example, the reaction is generally carried out in a polar aprotic solvent with an excess of the silylating reagent, 2.2 to 4 equivalents, and an excess relative to the silylating reagent of some nitrogen-containing compound such as imidazole. Silylation is usually carried out between 0° and 50° C.

Preferably, 6 equivalents imidazole and about 3 equivalents of t-butyldimethylsilyl chloride will be added to dry dimethylformamide solution of the hydroxy acid salt and stirred overnight at about room temperature. Preferably, completion of the reaction will be confirmed by tlc. This reaction gives the silyl ether as well as the silyl ester of the acid. Because the silyl ester is not desired, it is hydrolyzed in situ without being isolated by adding water to the reaction pot and then recovering the silyl ether compound in its free acid form.

The resulting free acid, represented by formula 4, is then converted to the aldehyde of formula 7. This can be accomplished by any number of appropriate methods, four of which are set out herein to exemplify the preferred methods. In one instance, formula 4 is esterified to give formula 5 which is then reduced to give the alcohol of formula 6, that being oxidized to the aldehyde of formula 7. A second alternative is to reduce the free acid of formula 4 to the alcohol of formula 6 and then oxidize the alcohol to the aldehyde (formula 7). Alternative three comprises esterifying the free acid of formula 4 and then reducing the ester directly to the aldehyde of formula 7. The fourth alternative is to first convert the free acid to the acid halide (acyl chloride) and then effect a Rosenmund redunction to form the aldehyde.

In the first alternative, the first step is to esterify the free acid by standard esterification procedures using, for example, either an alkyl iodide or a diazoalkane reagent. The words alkyl and alkane here have the same definition as that set forth above for lower alkyl.

When the reagent is an alkyl iodide, preferably methyl iodide, the reaction is carried out in an aprotic solvent such as dimethylformamide or dimethylacetamide containing a weak base such as sodium hydrogen carbonate. A large excess of the alkyl iodide is used, for example about 7-10 equivalents and corresponding large equivalents of base. The reaction is preferably carried out under an inert atmosphere, e.g. nitrogen and at a slightly elevated temperature not to exceed the boiling point of the alkyl iodide employed. If the reagent is methyl iodide, the reaction is preferably carried out at a temperature of about 40°-45° C. A number of hours are usually required to effect the reaction, usually 16 to 24 hours. Completion of the reaction can be confirmed by tlc. If the reaction is not complete after the initial reaction period, an additional one equivalent of the alkyl iodide and a corresponding amount of base are added and the reaction continued as before. This procedure is repeated as often as necessary to complete the reaction.

If a diazoalkane is used, preferably diazomethane, the reaction is carried out using standard procedures for generating diazomethane and for reacting it with the free acid. See F. Arndt, Org. Syn. Coll. Vol II, 165 (1943) and H. von Pechmann, Chem. Ber. 27, 1888 (1894) and 28, 855 (1895).

In the second step of the first alternative, reduction of the carboxylic acid ester to the alcohol (formula 6) is effected by a metal hydride such as diisobutylaluminum hydride, lithium aluminum hydride or the like. The reaction is carried out in a solvent compatible with the selected reducing agent and preferably under an inert atmosphere and at a temperature of less than 50° C. for a period of up to about 4 hours.

When the reducing agent is diisobutylaluminum hydride, the reaction is carried out in toluene, benzene or a similar nonpolar solvent. The diisobutylaluminum hydride in toluene is added to a cooled solution of the carboxylic acid ester after which the reaction solution is allowed to come to room temperature wherein the reaction is usually complete after 30-45 minutes. A nominal 2.5 equivalents of diisobutylaluminum hydride is employed to effect the reduction. The reaction can be monitored by tlc and, if not complete, additional hydride is added and stirring continued for an another 30 minutes or so. Unreacted hydride is decomposed by adding water and an alkali metal salt such as sodium fluoride or sodium sulfate.

Alternatively, the carboxylic acid ester may be reduced to the alcohol using lithium aluminum hydride in a polar solvent such as ethyl ether, tetrahydrofuran or the like. Lithium aluminum hydride reduction is effected using the same ratio of materials and same reaction conditions as recited above for diisobutylaluminum hydride.

Oxidization of the alcohol to the aldehyde is carried out by means of a mild oxidizing reagent. Any one of a number of mild oxidizing reagents may be used to effect this oxidation but it is preferred to use chromium (VI) trioxide, pyridinium dichromate, pyridinium chlorochromate or the like but preferably chromium trioxide, in the presence of pyridine, hexamethylphosphoric triamide, 3,5-dimethylpyrazole or the like, preferably pyridine, or pyridinium chlorochromate with sodium acetate, and an organic solvent, e.g., dichloromethane, dichloroethane, and the like preferably, dichloromethane or mixtures thereof at a temperature from about $-10°$ C. to about 30° C., preferably about 15° C. to about 25° C., for about 30 minutes to about 2 hours, preferably about 15 minutes to about 45 minutes, to obtain the aldehyde of formula 7. Advantageously, this reaction is carried out under anhydrous conditions under an inert atmosphere, e.g., nitrogen.

Alternative two is effected by simply reducing the free acid directly to the alcohol and then oxidizing that compound to the aldehyde of formula 7. The first step, reduction of the acid to the alcohol, is accomplished by means of borane methyl sulfide. In this reaction, the methyl ester is dissolved in a polar solvent, the solution stabilized in a bath at between about 0°-25° C. and the system purged with dry nitrogen. Borane methyl sulfide, about 3 equivalents is then added dropwise with stirring after which stirring is continued for up to about 6 hours, preferably about 3.5 hours to effect the reaction.

Having obtained the alcohol, it is then oxidized to the aldehyde in the manner set forth above for oxidizing formula 6 to formula 7.

The third alternative comprises first esterifying the free acid of formula 4 by the methods described above and then reducing the ester, formula 5, directly to the aldehyde by means of diisobutylaluminum hydride at low temperature. The reaction is effected using the same ratio of reactants given above, but in this instance the reaction is carried out at a temperature of about $-70°$ C. or thereabouts.

In the fourth alternative, the free acid is reduced to the aldehyde by first converting the acid to its acid halide (chloride) by reacting the acid with thionyl chloride, phosphorus trichloride or oxalyl chloride at a temperature range between 0° and 30° C. and then carrying out a Rosenmund reduction with $H_2$ and Palladium on barium sulfate at a temperature between 0° and 50° C., or its equivalent.

Formation of the propargyl alcohols, formula 8, is effected by means of a metal acetylide in an appropriate anhydrous organic solvent such as a halogenated alkane, an ether, a hydrocarbon or the like, preferably under an inert atmosphere such as nitrogen. To a preformed solution of aldehyde in a solvent such as methylene chloride, dichloroethane, tetrahydrofuran, diethyl ether, toluene or the like, preferably methylene chloride, is added an excess of a metal acetylide reagent, exemplified by ethynyl magnesium chloride, ethynyl magnesium bromide, ethynyl magnesium iodide, lithium acetylide ethylene diamine complex and ethynyl lithium, under nitrogen. The preferred metal acetylide is ethynyl magnesium chloride. The reaction is carried out at a temperature between 0° and 50° C., preferably between 20°–30° C., until the reaction is complete (which can be confirmed by tlc), usually within 30 minutes, most usually within 5–10 minutes.

The mixture of propargyl alcohol epimers may be separated into fractions containing a single pure propargylic epimer by chromatographic means, for example, silica gel tlc or column chromatography with varying mixtures of moderately polar solvents in non-polar solvents.

In case the mixtures of allene isomers (formulas Ia and Ib, or formulas Ia' and Ib') or mixtures of all four components are desired, this separation step is omitted.

Conversion of the propargyl alcohol to the allene may be carried out by any reaction which effects a stereospecific homologation/rearrangement. By this means, a single propargyl alcohol epimer can be converted to a single corresponding allenyl stereoisomer. Herein it is preferred to effect this rearrangement by means of a Claisen type rearrangement employing a lower trialkyl orthoacetate and a catalytic amount of a low molecular weight alkanoic acid, for example, acetic acid, propionic acid or the like. In this instance, a catalytic amount of acid is some amount less than 5% by volume relative to the volume of trialkyl orthoacetate.

The trialkyl orthoacetates which may be used are illustrated by trimethyl or triethyl orthoacetate and the like. The propargylic alcohol is dissolved in the trialkyl orthoacetate, preferably under nitrogen, along with a catalytic amount of alkanoic acid, usually about a 1% volume relative to the orthoacetate. The orthoester reacts with the propargyl alcohol to give a mixed trialkylorthoester which is not isolated but caused to rearrange in situ by heating the pot. The reaction flask is immersed in a preheated oil bath, for example one at about 150°–250° C., and stirred for a short period, about 30 minutes while maintaining the pot temperature between about 100°–130° C., preferably between about 110°–120° C. During the heating period, a mixture of orthoacetate and alkanoic acid, in the same ratio noted above, is added to the system while concurrently distilling out of the reaction system an equivalent volume of trialkyl orthoester-alkanol-acid. The reaction bath is preferably maintained at a temperature between about 170°–175° C. during the distillation process. The resulting product is the ester of formula 9.

To obtain the final product, it is necessary to add one carbon between the allene group and the acid function of formula 9 (homologation) in a manner which will not affect the stereochemistry of the allene or other sites on the molecule. The desired homologue is represented by formula 13. This homologation may be accomplished by a number of methods known in the art. The preferred methods employ a strong base in the last step of the homologation which will simultaneously cleave the $R^2$ group, giving the compounds of formula 13. Other reaction sequences require treatment with base after the homologue is formed in order to obtain the C-9 hydroxyl group of formula 13.

The alkyl ester generated by the Claisen rearrangement may be homologated by reducing the ester to its corresponding primary alcohol by some appropriate reducing reagent such as a metal hydride, e.g. lithium aluminum hydride, diisobutylaluminum hydride or the like. This alcohol is then converted to some functional group which is a good leaving group and then treated with an alkali metal cyanide, followed by treatment with a strong base to effect hydrolysis of both the nitrile and the $R^2$ group of C-9.

The leaving group to which the alcohol is converted may be, for example a halo group such as bromo or chloro or a sulfonyl ester. The alcohol is converted to the corresponding halo compound by a variety of methods known in the art. This product is then treated with cyanides such as alkali metal cyanide, for example sodium or potassium cyanide to make the nitrile. The nitrile is then hydrolyzed by strong base, which also serves to hydrolyze the $R^2$ base-labile ether group.

Alternatively, the alcohol is treated with an alkyl or arylalkyl sulfonyl ester forming reagent in preparation for making the nitrile. Such reagents are preferably methanesulfonyl chloride or p-toluenesulfonyl chloride or a similar sulfonyl halide. The sulfonyl ester is converted to the nitrile by means of an alkali metal cyanide salt, preferably sodium or potassium cyanide. This nitrile is then treated with strong base to effect formation of the acid while simultaneously hydrolyzing the $R^2$ group, which gives the compound of formula 13.

Another alternative is to reduce the ester function of formula 9 to an aldehyde, carry out a Wittig reaction, hydrolyze, and oxidize the resulting homologated aldehyde and then treat the resulting acid with base to effect hydrolysis of the $R^2$ group. In this sequence, the ester of formula 9 is reduced to its corresponding alcohol and oxidized to the aldehyde. Alternatively, the ester may be reduced directly to the aldehyde using diisobutylaluminum hydride at low temperature, e.g. $-70°$ C. The resulting aldehyde is then treated with the phosphorus ylide (phenyl)$_3$P=CHOCH$_3$ and then Hg(OAc)$_2$/KI to give the aldehyde homologue of formula 14. This aldehyde is treated with a mild oxidizing agent, one like the ones noted herein above, to obtain the protected acid. This protected acid is then treated with a dilute solution of a strong base to effect hydrolysis of the $R^2$ group. A full description of the base hydrolysis conditions is given herein below.

A third alternative is the Arndt-Eistert synthesis. For example, the ester of formula 9 is converted to the acid halide (chloride) by means of oxalyl chloride or thionyl chloride and then treated with diazomethane to give the diazoketone. The diazoketone is then rearranged to the homologated acid using silver oxide and water. This acid is then treated with base to hydrolyze the $R^2$ group giving the compound of formula 13.

The preferred method for converting formula 9 to its homologue, formula 13, is to first reduce the ester of formula 9 to its corresponding alcohol, form a sulfonyl ester of the alcohol, treat the sulfonyl ester with an alkali metal cyanide to obtain the nitrile, and convert the nitrile to the acid by base hydrolysis while simultaneously hydrolyzing the $R^2$ base-labile ether group.

In the preferred sequence, the acid ester of formula 9 is reduced to its corresponding alcohol by means of a metal hydride under anhydrous conditions, preferably under an inert atmosphere. A dry aprotic polar solvent such as absolute diethyl ether or the like is placed under a dry inert atmosphere and a reducing agent, for example a metal hydride such as lithium aluminum hydride (LAH) or the like, is added (2.2 to 4 equivalents) followed by the allenic ester. It is preferred to mix the several reaction ingredients at a reduced temperature, about 0°–15° C., and then reflux the solution for 10–30 minutes or until tlc indicates the reaction is complete.

When reduction is complete, the reaction mixture is again cooled to between 0°–15° C. and excess reagent (LAH) is reacted with a carbonyl-containing compound such as acetone or ethyl acetate thereby moderating subsequent and complete decomposition; complete decomposition follows addition of an aqueous complexing agent such as potassium sodium tartrate or a similar aluminum complex-forming salt.

In order to prepare the nitrile, the primary alcohol made as per the preceding paragraph is first converted to a alkyl- or arylalkylsulfonyl ester, for example the methanesulfonyl ester or p-toluenesulfonyl ester derivatives. The allenyl alcohol, dissolved in an anhydrous polar organic solvent such as a halogenated alkane, i.e. methylene chloride, dichloroethane and the like is introduced into a reaction flask along with an anhydrous trialkylamine such as triethylamine. The reaction flask is purged with dry nitrogen and the reaction mixture cooled to between about −40° and 25° C. The sulfonyl ester-forming reagent, e.g. methanesulfonyl chloride, dissolved in the anhydrous organic solvent is then added with stirring while maintaining the temperature of the reaction mixture at between about −40° to −20° C., preferably between −30° to −20° C. About a two fold molar excess of the ester-forming reagent is used. When addition of the sulfonyl ester-forming reagent is completed, about 15–30 minutes, the reaction mixture is stirred at between about −30° to −10° C. until the reaction is complete as can be indicated by tlc. When the reaction is completed, the cooling bath is removed and additional trialkylamine is added, predissolved in the organic solvent. A solution of aqueous sodium bicarbonate or a similar base is then added with vigorous stirring in order to decompose excess ester-forming reagent.

The nitrile is formed by means of an alkali metal cyanide, most preferably potassium cyanide. The reaction is carried out in a polar solvent, for example, dimethyl sulfoxide, under an inert atmosphere at a temperature between 50°–120° C. for up to an hour. Dry conditions are preferred.

The metal cyanide, about 5–8 equivalents, is first placed in a flask under an inert atmosphere such as nitrogen. Solvent is added and the flask placed in a bath preheated to about 75°–80° C. The intermediate, dissolved in the reaction solvent, is then added. Heating and stirring is continued for up to 2 hours, preferably 1 hour or until completion of the reaction as indicated by tlc.

Hydrolysis of the nitrile by base gives the salt (—COOM of formula 13), which may be acidified to obtain the free acid, and at the same time deprotects the C-9 hydroxy group, which, as noted above is a base-labile ether. These hydrolysis are effected with a dilute solution of a strong base such as one of the alkali metal hydroxide bases, e.g. lithium hydroxide, sodium hydroxide, potassium hydroxide and the like. A dilute solution is one which has a concentration of 0.05 to 2M., preferably about 0.5M. An appropriate solvent is, for example, 2-methoxyethanol or a similar polar solvent which is miscible with water. Preferably, an inert atmosphere is maintained. In terms of temperature and time the reaction is effected by heating the solvent to reflux for up to about 72 hours.

Preferably these hydrolysis will be effected by charging a reaction flask with the solvent and reactant, adding the base, predissolved in water, and then purging the system with nitrogen. The reaction mixture is then refluxed for about 60 hours. The cooled reaction mixture is then neutralized before isolation of the 9-hydroxy-1-acid product.

The acids of formulas 13 and 15 are esterified by the same procedures set forth herein above for esterifying formula 4.

Oxidation of the C-9 hydroxyl group is effected by a mild oxidizing agent such as those set forth herein above in the discussion relating to the oxidation of formula 6. Preferably, the oxidizing reagent will be chromium trioxide (4.5–10 equivalents) and 3,5-dimethylpyrazole or Collins reagent (chromium trioxide and pyridine), the reaction being carried out under an inert atmosphere in a polar aprotic solvent. Reagens are combined with solvent at reduced temperature, about −30° C. to −10° C. with stirring to effect thorough mixing of the reagents. The alcohol is then added in additional solvent, the initial reduced temperature being maintained during the addition and for the remainder of the reaction period, usually about 1 to 2 hours. Preferably the reaction will be carried out in methylene chloride under dry nitrogen for a period of about 1 hour.

Hydrolysis of the C-11 and C-15 blocking groups is effected by acid, for example, a alkanoic acid of 1 to 6 carbon atoms, or a hydrogen halide.

When acetic acid is used, standard procedures well known in the art may be used. For example, the standard hydrolysis procedure uses acetic acid and a polar solvent such a tetrahydrofuran or the like. The alkyl ester, glacial acetic acid, water and organic solvent are mixed in a flask under nitrogen and heated at low temperature, between about 20°–60° C., preferably 40° C. for up to 16 hours, preferably 12 hours. The preferred reaction medium is 85–95 w/v% of 20–60 w/v% of aqueous glacial acetic acid with 5–15 w/v% of an organic solvent. Most preferably, the reaction medium is 60 w/v% of water, 30 w/v% of acetic acid and 10 w/v% of tetrahydrofuran.

Alternatively, hydrolysis of the ether groups may be effected by a hydrogen halide, preferably an aqueous solution of the acid dispersed in a water immiscible solvent, preferrably with a scavenging agent to react with the released blocking groups, the reaction being effected at a temperature between −40° to 50° C. over a period of about 5 minutes to 4 hours. This method comprises stirring an aqueous solution of hydrogen halide with a water immiscible solvent in which the intermediate has been dissolved. The hydrogen halide may be hydrogen fluoride, hydrogen chloride, hydrogen bromide or hydrogen iodide. The acid should be present in a slight molar excess, for example about at least 2.05 equivalent of acid, though the reaction can be effected by using a large excess of acid, ie. up to 10 equivalents or more. Preferably 2.05 to 3.0 equivalents will be used, most preferably about 2.5 equivalents. Any water immiscible organic solvent may be used but it is preferred to use a halogenated hydrocarbon such as, for example, methylene chloride, dichloroethane and the like. To trap the released blocking group, a reactive scavenging material is added to the reaction mixture. This scavenging material is preferably a mercaptan, for example mercaptoethanol. The scavenging material is present in an amount of 2.0 to 3.0 equivalents, preferably about 2.0 equivalents. The reaction is complete in about 30–60 minutes at a temperature between about −30° to 50° C., preferably 10°–50° C.

When the R allene steveoisomer of formula I'

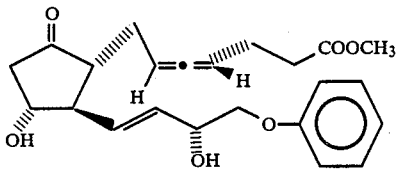

is prepared, removal of the solvent under reduced pressure affords the product as an oil. The oily material spontaneously crystallizes when it is cooled to a lower temperature, preferably at a temperature between −20° to 0° C. Purification of the crystalline material can be effected using conventional recrystallization techniques.

The R allenic isomer of formula I' is extremely useful in the treating and prevention of gastric and duodenal ulcers.

The R allenic isomer of formula I' can be administered in a wide variety of dosage forms, either alone or in combination with other pharmaceutically compatible medicaments, in the form of pharmaceutical compositions suited for oral or parenteral administration or inhalation in the case of bronchodilators. This compound is typically administered as pharmaceutical compositions consisting essentially of the compound and a pharmaceutical carrier. The pharmaceutical carrier can be either a solid material, liquid or aerosol, in which the compound is dissolved, dispersed or suspended, and can optionally contain small amounts of preservatives and/or pH buffering agents. Suitable preservatives which can be used include, for example, benzyl alcohol or the like. Suitable buffering agents include, for example, sodium acetate and pharmaceutical phosphate salts or the like.

The liquid compositions can, for example, be in the form of solutions, emulsions, suspensions, syrups, or elixirs. The solid compositions can take the form of tablets, powders, capsules, pills or the like, preferably in unit dosage forms for simple administration or precise dosages. Suitable solid carriers include, for example, pharmaceutical grades of starch, lactose, sodium saccharine, talcum, sodium bisulfite or the like.

For inhalation administration, the R allenic isomer of formula I' can, for example, be administered as an aerosol comprising this compound in an inert propellant together with a cosolvent, e.g., methanol, together with optional preservatives and buffering agents. Additional general information concerning the inhalation administration of aerosols can be had by reference to U.S. Pat. Nos. 2,868,691 and 3,095,355.

The precise effective dosage of the R allene isomer of formula I' will vary depending upon the mode of administration, condition being treated and host.

To further illustrate and exemplify the practice of this invention, the following non-limiting Examples are provided.

EXAMPLE 1

(1α-Hydroxy-4α-(tetrahydropyran-2-yloxy)-3β-(3α-(tetrahydropyran-2-yloxy)-4-phenoxy-1(E)-buten-1-yl)cyclopent-2α-yl)acetic acid lactone A 1 liter round bottom flask equipped with a magnetic stirring bar and Drierite ® drying tube was charged with 16.5 g of (1α,4α-dihydroxy-3β-(3α-hydroxy-4-phenoxy-1(E)-buten-1-yl)-cyclopent-2α-yl)acetic acid lactone, 500 ml of methylene chloride, 8.8 ml of dihydropyran and a few crystals of p-toluenesulfonic acid.H₂O. This mixture was stirred at room temperature for 2 hours. Two drops of triethylamine were added and the solution stirred for 2 minutes. The reaction mixture was washed with 1×50 ml of saturated aqueous sodium chloride and dried over sodium sulfate. Evaporation of the solvent gave a residue which was taken up in a minimum amount of ethyl acetate and charged onto a 7.5 cm diameter column filled with 500 g of silica gel packed in pure hexane. The column was then eluted with a gradient of 20% to 40% ethyl acetate in hexane. Appropriate fractions were combined and stripped to dryness to afford the title compound.

Proceeding in a similiar manner, but substituting for the starting compound in the preceding paragraph the appropriately substituted phenoxylactone, the following compounds may be prepared:

(1α-hydroxy-4α-(tetrahydropyran-2-yloxy)-3β-(3α-(tetrahydropyran-2-yloxy)-4-(m-trifluoromethylphenoxy)-1(E)-buten-1-yl)cyclopent-2α-yl)acetic acid lactone;

(1α-hydroxy-4α-(tetrahydropyran-2-yloxy)-3β-(3α-(tetrahydropyran-2-yloxy)-4-(m-fluorophenoxy)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(o-fluorophenoxy)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(p-fluorophenoxy)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(p-chlorophenoxy)-(1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(o-chlorophenoxy)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(m-chlorophenoxy)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(m-bromophenoxy)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(o-bromophenoxy)-1(E)-buten-1-yl)cyclopent-2α-yl)acetic acid lactone;

(1α-hydroxy-4α-(tetrahydropyran-2-yloxy)-3β-(3α-(tetrahydropyran-2-yloxy)-4-(p-bromophenoxy)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(m-methylphenoxy)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(o-methylphenoxy)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(p-methylphenoxy)-1(E)-buten-1-yl)-cyclopent-2α-yl)acetic acid lactone;

(1α-hydroxy-4α-(tetrahydropyran-2-yloxy)-3β-(3α-tetrahydropyran-2-yloxy)-4-(m-methoxyphenoxy)-1(E)-buten-1-yl)-cyclopent-2α-yl)acetic acid lactone;

(1α-hydroxy-4α-(tetrahydropyran-2-yloxy)-3β-(3α-(tetrahydropyran-2-yloxy)-4-(o-methoxyphenoxy)-1(E)-buten-1-yl)-cyclopent-2α-yl)acetic acid lactone; and (1α-hydroxy-4α-(tetrahydropyran-2-yloxy)-3β-(3α-(tetrahydropyran-2-yloxy)-4-p-methoxyphenoxy)-1(E)-buten-1-yl)-cyclopent-2α-yl)acetic acid lactone.

EXAMPLE 2

Potassium (1α-hydroxy-4α-(tetrahydropyran-2-yloxy)-3β-(3α-tetrahydropyran-2-yloxy)-4-phenoxy-1(E)-(buten-1-yl)-cyclopent-2α-yl)-acetate A reaction flask equipped with a magnetic stirrer and reflux condenser topped with a nitrogen inlet was charged with 25 ml of tetrahydrofuran and 5 g of (1α-hydroxy-4α-(tetrahydropyran-2-yloxy)-3β-(3α-(tetrahydropyran-2-yloxy)-4-phenoxy-1(E)-buten-1-yl)-cyclopent-2α-yl)acetic acid lactone. The suspension was stirred until the reactant had dissolved during which time the flask was vacuum purged with nitrogen. A 3.82 ml aliquot of 2.91M KOH/H$_2$O was added and the reaction flask again vacuum purged with nitrogen. This solution was then refluxed under nitrogen until the reaction was completed (monitored by tlc). The cooled solution was stripped to dryness, dissolved in 50 ml of toluene and stripped to dryness under vacuum to provide the title compound.

Proceeding in a similiar manner, but replacing the starting material with an analog from Example 1, all compounds prepared as per Example 1 are converted to the corresponding potassium salt.

EXAMPLE 3

(1α-t-Butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)-acetic acid A 7.76 g aliquot of potassium (1α-hydroxy-4α-(tetrahydropyran-2-yloxy)-3β-(3α-(tetrahydropyran-2-yloxy)-4-phenoxy-1(E)-buten-1-yl)-cyclopent-2α-yl)acetate was introduced into a reaction flask and 25 ml of dry dimethylformamide added. Imidazole, 4.32 g, was added to the stirred mixture followed by a 4.7 aliquot of t-butyldimethylsilyl chloride. The reaction was stirred overnight at room temperature after which 5 ml of water was added with vigorous stirring for 30 to 45 minutes. The product was recovered by extraction with diethyl ether, followed by a saturated aqueous sodium chloride wash, after which the solution was dried over sodium sulfate and the solvent removed under reduced pressure. The residue was further purified by passing it through a 350 ml "C" sintered glass filter funnel packed with 95 g silica gel slurried in 10% v/v ethyl acetate/hexane, the free acid being eluted with 1 L of 10% ethyl acetate/hexane. Appropriate fractions were combined and the solvent removed to give the title compound.

By the same method, the compounds prepared in Example 2 are converted to the corresponding t-butyldimethylsilyl ether compounds.

EXAMPLE 4

Methyl (1α-t-butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)acetate Dry dimethylformamide, 80 ml, and 6.24 g of (1α-t-butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)acetic acid, 3.00 g NaHCO$_3$ and 12.01 g methyl iodide were introduced into a reaction flask equipped with a stirrer and reflux condenser topped with N$_2$/vac/septum inlet. The flask was vacuum purged five times with nitrogen and then heated to between 40°–45° C. and stirred overnight. Additional methyl iodide (1.46 g) was added and the reaction continued at 40°–45° C. over a second night. Water, 500 ml, was then added to the reaction mixture which was then extracted with 3×50 ml of methylene chloride. The combined methylene chloride layers were further diluted with an equal volume of hexane. The resulting organic layer was washed with water (2×50 ml), saturated sodium chloride (1×50 ml) and dried over sodium sulfate. Evaporation of the solvent afforded a residue which was further purified by silica gel column chromatography. The silica gel was prepared in 15% ethyl acetate/hexane and the compound eluted with that solvent mixture. Combined appropriate fractions were stripped to dryness to give the title compound.

Proceeding in the same manner, but substituting for the starting compound named herein, the compounds prepared in Example 3, each compound prepared in that Example may be converted to its methyl ester.

EXAMPLE 5

(1α-t-Butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)-2-ethanol-1-ol Into a reaction flask fitted with a N$_2$/vac/septum inlet was introduced 53 ml of dry toluene in which was dissolved 5.3 g of methyl (1α-t-butyldimethylsilyloxy-4α-(tetrahydropyran-2-yloxy)-3β-(3α-(tetrahydropyran-2-yloxy)-4-phenoxy-1(E)-buten-1-yl)cyclopent-2α-yl)acetate. The reaction was cooled in an ice bath and vacuum purged five times with nitrogen. Using a dry syringe transfer technique, 21.4 ml of diisobutylaluminum hydride, 1.0M in toluene, was placed in an addition funnel and added to the cool reaction solution over about 20 minutes. The ice bath was then removed and the reaction mixture checked by tlc after 30 minutes. If the reaction was not complete an additional 4.28 ml of the hydride solution was added. When reduction was complete, the reaction mixture was diluted with 26 ml of dry hexane and 4.32 g of sodium fluoride powder was added with vigorous stirring. A 1.39 ml aliquot of water was then added with stirring. After an additional 30–40 minutes had elapsed, during which stirring was continued, the reaction solution was filtered through celite and rinsed with 100 ml methylene chloride. The solvent was then stripped off under vacuum and the residue further purified by silica gel column chromatography. The title compound has the following $^1$H NMR spectral data:

| δ ppm | |
|---|---|
| 7.28 | 2H, t, J = 7.5 Hz, H-19 |
| 6.86–6.98 | 3H, m, H-18, 20 |
| 5.46–5.83 | 2H, m, H-13-14 |
| 4.92 | m, H-2' THP |
| 4.81 | m, H-2' THP |
| 4.67 | m, H-2' THP |
| 3.88 | 2H, m, H-6' THP |
| 3.47 | 2H, m, H-6' THP |
| 0.89 | 9H, s, t-butyl |
| 0.5 | s, silylmethyl |
| 0.7 | s, silylmethyl |
| 3.9–4.15 | 3H, m, H-11, 16 |
| 4.19 | 1H, m, H-9 |
| 4.52 | 1H, m, H-15 |
| 3.62 | 2H, m, H-6 |

Proceeding in a similar manner, compounds made in Example 4 may be transformed to their corresponding alcohol.

EXAMPLE 6

(1α-t-butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)-2-ethan-1-ol The following process is an alternative method for making the captioned alcohol.

A 1.08 g aliquot of (1α-t-butyldimethylsilyloxy-4α-(tetrahydropyran-2-yloxy)-3β-(3α-(tetrahydropyran-2-yloxy)-4-phenoxy-1(E)-buten-1-yl)cyclopent-2α-yl)acetic acid was weighed into a round bottom flask equipped with a stirrer and septum/N₂/vacuum inlet. Dry tetrahydrofuran, 11 ml, was added to dissolve the acetate. The flask was placed in a water bath at about 18°–20° C. and purged five times with dry nitrogen. Then 0.392 ml of borane methyl sulfide was added dropwise over 30 minutes. Stirring was then continued for about 3.5 hours. Methanol, 1 ml, was then added dropwise, gas evolution being controlled by the rate of addition. An additional 5 ml of methanol was then added, the solution then being stirred for another 30 minutes. The reaction mixture was then concentrated. The residue was dissolved in methanol and reconcentrated. The second concentrate was dissolved in 25 ml of diethyl ether and washed with 1×5 ml of water, 1×5 ml of saturated aqueous sodium bicarbonate, 1×5 ml of brine and dried over sodium sulfate. This dried solution was filtered and concentrated, giving a colorless oil.

The oil from above was further purified by percolating it through a column of 10 g of silica gel packed wet in 10% ethyl acetate/hexane. The product was eluted with successive portions of 200 ml 10% ethyl acetate/hexane, 200 ml of 20% ethyl acetate/hexane and 200 ml of 30% ethyl acetate/hexane while collecting 20 ml fractions. Fractions 12–30 were combined and the solvent removed in vacuo, giving the title product as a colorless oil.

EXAMPLE 7

(1α-t-Butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)acetaldehyde A reaction flask was fitted with an addition funnel and dry nitrogen inlet/outlet valves. 150 ml of anhydrous methylene chloride and 5.96 g of anhydrous chromium (VI) trioxide was placed in the flask. The flask was vacuum purged with dry nitrogen and cooled in an ice bath to approximately 15° C. To the flask was then added with vigorous stirring 9.46 g of anhydrous pyridine after which the reaction mixture was stirred vigorously under dry nitrogen at ambient temperature for 30 minutes. Dry celite (5.0 g) was then added under nitrogen followed by 4.7 g of (1α-t-butyldimethylsilyloxy-4α-(tetrahydropyran-2-yloxy)-3β-(3α-(tetrahydropyran-2-yloxy)-4-phenoxy-1(E)-buten-1-yl)cyclopent-2α-yl)-2-ethan-1-ol in 18.5 ml of anhydrous methylene chloride. The reaction solution was stirred for 15–20 minutes, or until tlc indicated the reaction was complete, at which time 12.5 g of pulverized sodium hydrogen sulfate monohydrate was added. After an additional 15 minutes of vigorous stirring, the reaction mixture was filtered and the retentate washed with methylene chloride (3×50 ml). The combined methylene chloride solutions were washed with 3×50 ml of water and the aqueous layer back extracted with 2×25 ml methylene chloride. The dried (anhydrous sodium sulfate) methylene chloride solution was stripped under vacuum to provide the title compound, having the following ¹H NMR spectral data:

| δ ppm | |
|---|---|
| 7.28 | 2H, t, J = 7.5 Hz, H-19 |
| 6.86–6.98 | 3H, m, H-18, 20 |
| 5.46–5.73 | 2H, m, H-13-14 |
| 4.95 | m, H-2' THP |
| 4.80 | m, H-2' THP |
| 4.67 | m, H-2' THP |
| 3.88 | 2H, m, H-6' THP |
| 3.47 | 2H, m, H-6' THP |
| 0.89 | 9H, s, t-butyl |
| 0.5 | s, silylmethyl |
| 0.7 | s, silylmethyl |
| 3.9–4.15 | 3H, m, H-11, 16 |
| 4.23 | 1H, m, H-9 |
| 4.50 | 1H, m, H-15 |
| 9.75 | 1H, m, H-6 |

By this means, the compounds prepared in the Examples 5 and 6 are converted to their corresponding acetaldehyde as illustrated by the following compounds:

(1α-t-butyldimethylsilyloxy-4α-(tetrahydropyran-2-yloxy)-3β-(3α-(tetrahydropyran-2-yloxy)-4-(m-trifluoromethylphenoxy)-1(E)-buten-1-yl)-cyclopent-2α-yl)acetaldehyde;

(1α-t-butyldimethylsilyloxy-4α-(tetrahydropyran-2-yloxy)-3β-(3α-(tetrahydropyran-2-yloxy)-4-(m-fluorophenoxy)-1(E)-buten-1-yl)-cyclopent-2α-yl)acetaldehyde;

(1α-t-butyldimethylsilyloxy-4α-(tetrahydropyran-2-yloxy)-3β-(3α-(tetrahydropyran-2-yloxy)-4-(o-fluorophenoxy)-1(E)-buten-1-yl)-cyclopent-2α-yl)acetaldehyde;

(1α-t-butyldimethylsilyloxy-4α-(tetrahydropyran-2-yloxy)-3β-(3α-(tetrahydropyran-2-yloxy)-4-(p-fluorophenoxy)-1(E)-buten-1-yl)-cyclopent-2α-yl)acetaldehyde;

(1α-t-butyldimethylsilyloxy-4α-(tetrahydropyran-2-yloxy)-3β-(3α-(tetrahydropyran-2-yloxy)-4-(p-chlorophenoxy)-1(E)-buten-1-yl)-cyclopent-2α-yl)acetaldehyde;

(1α-t-butyldimethylsilyloxy-4α-(tetrahydropyran-2-yloxy)-3β-(3α-(tetrahydropyran-2-yloxy)-4-(o-chlorophenoxy)-1(E)-buten-1-yl)-cyclopent-2α-yl)acetaldehyde;

(1α-t-butyldimethylsilyloxy-4α-(tetrahydropyran-2-yloxy)-3β-(3α-(tetrahydropyran-2-yloxy)-4-(m- chlorophenoxy)-1(E)-buten-1-yl)-cyclopent-2α-yl)acetaldehyde;

(1α-t-butyldimethylsilyloxy-4α-(tetrahydropyran-2-yloxy)-3β-(3α-(tetrahydropyran-2-yloxy)-4-(m-bromophenoxy)-1(E)-buten-1-yl)-cyclopent-2α-yl)acetaldehyde;

(1α-t-butyldimethylsilyloxy-4α-(tetrahydropyran-2-yloxy)-3β-(3α-(tetrahydropyran-2-yloxy)-4-(o-bromophenoxy)-1(E)-buten-1-yl)-cyclopent-2α-yl)acetaldehyde;

(1α-t-butyldimethylsilyloxy-4α-(tetrahydropyran-2-yloxy)-3β-(3α-(tetrahydropyran-2-yloxy)-4-(p-bromophenoxy)-1(E)-buten-1-yl)-cyclopent-2α-yl)acetaldehyde;

(1α-t-butyldimethylsilyloxy-4α-(tetrahydropyran-2-yloxy)-3β-(3α-(tetrahydropyran-2-yloxy)-4-(p-methylphenoxy)-1(E)-buten-1-yl)-cyclopent-2α-yl)acetaldehyde;

(1α-t-butyldimethylsilyloxy-4α-(tetrahydropyran-2-yloxy)-3β-(3α-(tetrahydropyran-2-yloxy)-4-(o-methylphenoxy)-1(E)-buten-1-yl)-cyclopent-2α-yl)acetaldehyde;

(1α-t-butyldimethylsilyloxy-4α-(tetrahydropyran-2-yloxy)-3β-(3α-(tetrahydropyran-2-yloxy)-4-(m-methylphenoxy)-1(E)-buten-1-yl)-cyclopent-2α-yl)acetaldehyde;

(1α-t-butyldimethylsilyloxy-4α-(tetrahydropyran-2-yloxy)-3β-(3α-(tetrahydropyran-2-yloxy)-4-(m-methoxyphenoxy)-1(E)-buten-1-yl)-cyclopent-2α-yl)acetaldehyde;

(1α-t-butyldimethylsilyloxy-4α-(tetrahydropyran-2-yloxy)-3β-(3α-(tetrahydropyran-2-yloxy)-4-(o-methoxyphenoxy)-1(E)-buten-1-yl)-cyclopent-2α-yl)acetaldehyde; and (1α-t-butyldimethylsilyloxy-4α-(tetrahydropyran-2-yloxy)-3β-(3α-(tetrahydropyran-2-yloxy)-4-(p-methoxyphenoxy)-1(E)-buten-1-yl)-cyclopent-2α-yl)acetaldehyde.

EXAMPLE 8

(1α-t-Butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)acetaldehyde Alternatively, the captioned aldehyde can be made directly from the methyl ester of Example 4 by means of the following reaction. A 100 mg aliquot of methyl-(1α-butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)acetate was weighed into a round bottom flask fitted with a stirrer and septum/N₂/vacuum inlet. Toluene, 1 ml, was added and the system vacuum purged with N₂ five times. This solution was cooled in a dry ice/isopropanol bath and 0.324 ml of 1M diisobutylaluminum hydride in toluene added was added dropwise over about 8 minutes. This solution was stirred under nitrogen at −78° C. for 2 hours and then diluted with 10 ml of diethyl ether. The cold bath was removed and 4 ml of saturated aqueous ammonium chloride added, the resulting solution being stirred vigorously for 30 minutes and then filtered through celite. The aqueous layer was extracted with diethyl ether, the extracts were combined, dried, and the solvent removed in vacuo to give the title compound as an oil.

This reaction may be used to convert any other methyl ester prepared in Example 4 to its corresponding aldehyde, as illustrated by the following compounds:

(1α-t-butyldimethylsilyloxy-4α-(tetrahydropyran-2-yloxy)-3β-(3α-(tetrahydropyran-2-yloxy)-4-(p-hexylphenoxy)-1(E)-buten-1-yl)-cyclopent-2α-yl)acetaldehyde;

(1α-t-butyldimethylsilyloxy-4α-(tetrahydropyran-2-yloxy)-3β-(3α-(tetrahydropyran-2-yloxy)-4-(o-hexylphenoxy)-1(E)-buten-1-yl)-cyclopent-2α-yl)acetaldehyde;

(1α-t-butyldimethylsilyloxy-4α-(tetrahydropyran-2-yloxy)-3β-(3α-(tetrahydropyran-2-yloxy)-4-(m-hexylphenoxy)-1(E)-buten-1-yl)-cyclopent-2α-yl)acetaldehyde;

(1α-t-butyldimethylsilyloxy-4α-(tetrahydropyran-2-yloxy)-3β-(3α-(tetrahydropyran-2-yloxy)-4-(m-hexyloxyphenoxy)-1(E)-buten-1-yl)-cyclopent-2α-yl)acetaldehyde;

(1α-t-butyldimethylsilyloxy-4α-(tetrahydropyran-2-yloxy)-3β-(3α-(tetrahydropyran-2-yloxy)-4-(l-hexyloxy-phenoxy)-1(E)-buten-1-yl)-cyclopent-2α-yl)acetaldehyde; and (1α-t-butyldimethylsilyloxy-4α-(tetrahydropyran-2-yloxy)-3β-(3α-(tetrahydropyran-2-yloxy)-4-(p-hexyloxy-phenoxy)-1(E)-buten-1-yl)-cyclopent-2α-yl)acetaldehyde.

EXAMPLE 9

(1α-t-Butyldimethylsiloxy-4α-(tetrahydropyran-2-yloxy)-3β-(3α-(tetrahydropyran-2-yloxy)-4-phenoxy-1(E)-buten-1-yl)-cyclopent-2α-yl)-1-but-3-yn-2-ol To a reaction flask fitted with a pressure equalizing addition funnel and dry nitrogen inlet/outlet valves was added 4.65 gm (7.9 mM) of (1α-t-butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)acetaldehyde in 30 ml of anhydrous methylene chloride. The flask was vacuum purged with dry nitrogen and cooled to approximately 15° C. while stirring vigorously. To this solution was added 9.0 ml of a 1.25M ethynyl magnesium chloride solution in tetrahydrofuran after which the pot was stirred for 5–10 minutes at ambient temperature or until the reaction was complete as indicated by tlc. Then 30 ml of methylene chloride and 50 ml of warm (35° C.) filtered, saturated aqueous ammonium chloride was added and the solution stirred vigorously for 5–10 minutes. A 50 ml aliquot of warm water (35° C.) was added with an additional 5–10 minute stirring time. This solution was then filtered and the retentate washed with 50 ml of methylene chloride and the aqueous layer extracted with 2 additional 15 ml portions of methylene chloride. The combined methylene chloride extracts were mixed with 100 ml of water, the methylene chloride layer being removed and the aqueous layer back-extracted with 20 ml of methylene chloride. The combined methylene chloride solutions were dried over anhydrous sodium sulfate, filtered and the solvent removed under reduced pressure to afford the title compound as an oily residue.

The individual isomers may be separated as follows: the oil from above was chromatographed on a silica gel column made up in hexane, the product being eluted with 5%–15% ethyl acetate/hexane in 5% step increments of ethyl acetate concentration. This separation technique afforded two fractions, each comprising a stereochemically pure propargyl alcohol.

A ¹³C NMR spectrum was measured for the purified, but unseparated mixture of the two stereoisomers of (1α,4α-dihydroxy-3β-(3α-hydroxy-4-phenoxy-1(E)- buten-1-yl)-cyclopent-2α-yl)-1-but-3-yn-2-ol and for the two individual isomers after chromatographic separation. The protecting groups at C-9, C-11 and C-15 were hydrolyzed by acid before measuring the NMR spectra. Acid hydrolysis was effected by acetic acid using the conditions and reagents set out below in Example 17 though the reagents and conditions of Example 18 could also be used for this purpose. The spectra were measured in $CDCl_3/CD_3OD$ on a Bruker WM 300 spectrometer operating at 75.473 MHz using a spectral width of 18,500 Hz, 40° flip angles and 16K data tables, zero filled to 32K after application of a 1.0 Hz line broadening giving a digital resolution in the frequency domain of 0.03 ppm. Tetramethylsilane was used as the internal standard for all spectra.

The resulting spectral data are set out in the following charts. The chemical shift is given for each carbon in the formula. Numbers 1 to 16 signify the particular carbon in question relative to formula I. Numbers 17 to 20 signify the oxygen-substituted, ortho, meta and para carbons respectively of the phenoxy moiety. In this Example the first three carbons are not present so there is no chemical shift recorded, dsignated by the letters NA for "not applicable." The separated isomers are designated "1" and "2" solely for the purpose of identification.

| ISOMER MIXTURE | | |
|---|---|---|
| 1. NA | 6. 60.65, 61.37 | 11. 76.86, 76.95 |
| 2. NA | 7. 34.28, 35.71 | 12. 55.47, 55.76 |
| 3. NA | 8. 45.42, 47.33 | 13. 130.89 |
| 4. 72.68, 73.39 | 9. 71.84, 71.96 | 14. 134.86, 134.95 |
| 5. 84.38, 85.17 | 10. 42.10, 42.19 | 15. 70.90, 70.97 |
| 16. 71.65 | | |
| 17. 158.56 | | |
| 18. 114.75 | | |
| 19. 129.56 | | |
| 20. 121.20 | | |
| ISOMER 1 | | |
| 1. NA | 6. 60.69 | 11. 77.03 |
| 2. NA | 7. 34.20 | 12. 55.64 |
| 3. NA | 8. 45.55 | 13. 130.70 |
| 4. 73.36 | 9. 71.89 | 14. 134.92 |
| 5. 84.27 | 10. 42.01 | 15. 70.92 |
| 16. 71.64 | | |
| 17. 158.54 | | |
| 18. 114.70 | | |
| 19. 129.56 | | |
| 20. 121.20 | | |
| ISOMER 2 | | |
| 1. NA | 6. 61.36 | 11. 76.85 |
| 2. NA | 7. 35.71 | 12. 55.82 |
| 3. NA | 8. 47.43 | 13. 130.86 |
| 4. 72.54 | 9. 71.94 | 14. 134.86 |
| 5. 85.18 | 10. 42.10 | 15. 70.87 |
| 16. 71.66 | | |
| 17. 158.57 | | |
| 18. 114.75 | | |
| 19. 129.56 | | |
| 20. 121.21 | | |

By using the same reagents and conditions and repeating the chromatographic separation outlined here, the acetaldehydes prepared in Examples 7 and 8 are converted to the corresponding alcohol and may be separated into the individual stereoisomers. The following list of compounds illustrates some of these compounds:

(1α-t-butyldimethylsilyloxy-4α-(tetrahydropyran-2-yloxy)-3β-(3α-(tetrahydropyran-2-yloxy)-4-(m-trifluoromethylphenoxy)-1(E)-buten-1-yl)-cyclopent-2α-yl)-1-but-3-yn-2-ol;

(1α-t-butyldimethylsilyloxy-4α-(tetrahydropyran-2-yloxy)-3β-(3α-(tetrahydropyran-2-yloxy)-4-(m-fluorophenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-(tetrahydropyran-2-yloxy)-4-(o-fluorophenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-(tetrahydropyran-2-yloxy)-4-(p-fluorophenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-(tetrahydropyran-2-yloxy)-4-(p-chlorophenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-(tetrahydropyran-2-yloxy)-4-(o-chlorophenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-(tetrahydropyran-2-yloxy)-4-(m-chlorophenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-(tetrahydropyran-2-yloxy)-4-(m-bromophenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-(tetrahydropyran-2-yloxy)-4-(o-bromophenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-(tetrahydropyran-2-yloxy)-4-(p-bromophenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-(tetrahydropyran-2-yloxy)-4-(p-methylphenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-(tetrahydropyran-2-yloxy)-4-(o-methylphenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-(tetrahydropyran-2-yloxy)-4-(m-methylphenoxy)-1(E)-buten-1-yl)-cyclopent-α-yl)1-but-3-yn-2-ol;

(1α-t-butyldimethylsilyloxy-4α-(tetrahydropyran-2-yloxy)-3β-(3α-(tetrahydropyran-2-yloxy)-4-(m-methoxyphenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-(tetrahydropyran-2-yloxy)-4-(o-methoxyphenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-(tetrahydropyran-2-yloxy)-4-(p-methoxyphenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-(tetrahydropyran-2-yloxy)-4-(p-hexylphenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-(tetrahydropyran-2-yloxy)-4-(o-hexylphenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-tetrahydropyran-2-yloxy)-4-(m-hexylphenoxy)-1(E)-buten-1-yl)-cyclopent-2α-yl)1-but-3-yn-2-ol;

(1α-t-butyldimethylsilyloxy-4α-(tetrahydropyran-2-yloxy)-3β-(3α-(tetrahydropyran-2-yloxy)-4-(m-hexyloxy-phenoxy)-1(E)-buten-1-yl)-cyclopent-2α-yl)-1-but-3-yn-2-ol;

(1α-t-butyldimethylsilyloxy-4α-(tetrahydropyran-2-yloxy)-3β-(3α-(tetrahydropyran-2-yloxy)-4-(o-hexyloxy-phenoxy)-1(E)-buten-1-yl)-cyclopent-2α-yl)-1-but-3-yn-2-ol; and (1α-t-butyldimethylsilyloxy-4α-(tetrahydropyran-2-yloxy)-3β-(3α-(tetrahydropyran-2-yloxy)-4-(p-hexyloxy-phenoxy)-1(E)-buten-1-yl)-cyclopent-2α-yl)1-but-3-yn-2-ol.

EXAMPLE 10

Ethyl-(1α-t-butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)-6-hexa-3,4-dienoate A three necked flask was fitted with a nitrogen inlet needle, pressure equalized addition funnel and vacuum type distillation head fitted with a cold finger condenser. A solution of 3.18 g of one isomer of (1α-t-butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)-1-but-3-yn-2-ol in 18 ml of triethyl orthoacetate, to which was added 0.18 ml of glacial acetic acid, was introduced into the reaction vessel. Dry nitrogen was bubbled through the reaction solution which was heated with stirring in a 170°–175° C. oil bath. Over a period of 30–35 minutes an additional 0.1 ml of glacial acetic acid and 6.0 ml of triethyl orthoacetate was added to the reaction solution. A 6 ml volume of triethyl orthoacetate-ethanol-acetic acid was distilled out of the reaction system after which the hot reaction solution was transferred to a second flask and 12.0 ml of toluene added to the reaction solution. The reagents were then distilled off under reduced pressure to give an oil. Toluene was added to this oil after which the toluene was removed under reduced pressure to afford the title compound having the following $^1$H NMR spectral data:

| δ ppm | |
|---|---|
| 7.28 | 2H, t, J = 7.5 Hz, H-19 |
| 6.86–6.98 | 3H, m, H-18, 20 |
| 5.43–5.82 | 2H, m, H-13-14 |
| 4.98 | m, H-2' THP |
| 4.81 | m, H-2' THP |
| 4.67 | m, H-2' THP |
| 3.88 | 2H, m, H-6' THP |
| 3.47 | 2H, m, H-6' THP |
| 0.89 | 9H, s, t-butyl |
| 0.5 | s, silylmethyl |
| 0.7 | s, silylmethyl |
| 3.9–4.15 | 3H, m, H-11, 16 |
| 4.19 | 1H, m, H-9 |
| 4.52 | 1H, m, H-15 |
| 5.22 | 2H, m, H-4, 6 |
| 4.13 | 2H, q J = 7.0, OCH$_2$ |
| 3.01 | 2H, m, H-3 |
| 1.27 | 2H, m, CH$_3$ |

The crude allenyl ester was then chromatographed on silica gel eluting with a gradient of hexane to 50% ethyl acetate/hexane to separate the allene from residual propargyl alcohol precursor.

Proceeding in the same manner, each of the individual isomers, or an unseparated mixture, of the compounds prepared in Example 7 and 8 are rearranged to their corresponding dienoate illustrated by the following compounds:

ethyl-(1α-t-butyldimethylsilyloxy-4α-(tetrapyran-2-yloxy)-3β-(3α-(tetrahydropyran-2-yloxy)-4-(m-trifluoromethylphenoxy)-1(E)-buten-1-yl)-cyclopent-2α-yl)-6-hexa-3,4-dienoate;

ethyl-(1α-t-butyldimethylsilyloxy-4α-(tetrapyran-2-yloxy)-3β-(3α-(tetrahydropyran-2-yloxy)-4-(m-fluorophenoxy)-1(E)-buten-1-yl)-cyclopent-2α-yl)1-6-hexa-3,4-dienoate;

ethyl-(1α-t-butyldimethylsilyloxy-4α-(tetrapyran-2-yloxy)-3β-(3α-(tetrahydropyran-2-yloxy)-4-(o-fluorophenoxy)-1(E)-buten-1-yl)-cyclopent-2α-yl)1-6-hexa-3,4-dienoate;

ethyl-(1α-t-butyldimethylsilyloxy-4α-(tetrapyran-2-yloxy)-3β-(3α-(tetrahydropyran-2-yloxy)-4-(p-fluorophenoxy)-1(E)-buten-1-yl)-cyclopent-2α-yl)1-6-hexa-3,4-dienoate;

ethyl-(1α-t-butyldimethylsilyloxy-4α-(tetrapyran-2-yloxy)-3β-(3α-(tetrahydropyran-2-yloxy)-4-(p-chlorophenoxy)-1(E)-buten-1-yl)-cyclopent-2α-yl)1-6-hexa-3,4-dienoate;

ethyl-(1α-t-butyldimethylsilyloxy-4α-(tetrapyran-2-yloxy)-3β-(3α-(tetrahydropyran-2-yloxy)-4-(o-chlorophenoxy)-1(E)-buten-1-yl)-cyclopent-2α-yl)1-6-hexa-3,4-dienoate;

ethyl-(1α-t-butyldimethylsilyloxy-4α-(tetrapyran-2-yloxy)-3β-(3α-(tetrahydropyran-2-yloxy)-4-(m-chlorophenoxy)-1(E)-buten-1-yl)-cyclopent-2α-yl)-1-6-hexa-3,4-dienoate;

ethyl-(1α-t-butyldimethylsilyloxy-4α-(tetrapyran-2-yloxy)-3β-(3α-(tetrahydropyran-2-yloxy)-4-(m-bromophenoxy)-1(E)-buten-1-yl)-cyclopent-2α-yl)1-6-hexa-3,4-dienoate;

ethyl-(1α-t-butyldimethylsilyloxy-4α-(tetrapyran-2-yloxy)-3β-(3α-(tetrahydropyran-2-yloxy)-4-(o-bromophenoxy)-1(E)-buten-1-yl)-cyclopent-2α-yl)1-6-hexa-3,4-dienoate;

ethyl-(1α-t-butyldimethylsilyloxy-4α-(tetrapyran-2-yloxy)-3β-(3α-(tetrahydropyran-2-yloxy)-4-(p-bromophenoxy)-1(E)-buten-1-yl)-cyclopent-2α-yl)1-6-hexa-3,4-dienoate;

ethyl-(1α-t-butyldimethylsilyloxy-4α-(tetrapyran-2-yloxy)-3β-(3α-(tetrahydropyran-2-yloxy)-4-(p-methylphenoxy)-1(E)-buten-1-yl)-cyclopent-2α-yl)1-6-hexa-3,4-dienoate;

ethyl-(1α-t-butyldimethylsilyloxy-4α-(tetrapyran-2-yloxy)-3β-(3α-(tetrahydropyran-2-yloxy)-4-(o-methylphenoxy)-1(E)-buten-1-yl)-cyclopent-2α-yl)1-6-hexa-3,4-dienoate;

ethyl-(1α-t-butyldimethylsilyloxy-4α-(tetrapyran-2-yloxy)-3β-(3α-tetrapyran-2-yloxy)-4-(m-methylphenoxy)-1(E)-buten-1-yl)-cyclopent-2α-yl)1-6-hexa-3,4-dienoate;

ethyl-(1α-t-butyldimethylsilyloxy-4α-tetrapyran-2-yloxy)-3β-(3α-(tetrahydropyran-2-yloxy)-4-(m-methoxyphenoxy)-1(E)-buten-1-yl)-cyclopent-2α-yl)1-6-hexa-3,4-dienoate;

ethyl-(1α-t-butyldimethylsilyloxy-4α-(tetrapyran-2-yloxy)-3β-(3α-(tetrahydropyran-2-yloxy)-4-(o-methoxyphenoxy)-1(E)-buten-1-yl)-cyclopent-2α-yl)1-6-hexa-3,4-dienoate;

ethyl-(1α-t-butyldimethylsilyloxy-4α-(tetrapyran-2-yloxy)-3β-(3α-(tetrahydropyran-2-yloxy)-4-(p-methoxyphenoxy)-1(E)-buten-1-yl)-cyclopent-2α-yl)1-6-hexa-3,4-dienoate;

ethyl-(1α-t-butyldimethylsilyloxy-4α-(tetrapyran-2-yloxy)-3β-(3α-(tetrahydropyran-2-yloxy)-4-(p-hexylphenoxy)-1(E)-buten-1-yl)-cyclopent-2α-yl)1-6-hexa-3,4-dienoate;

ethyl-(1α-t-butyldimethylsilyloxy-4α-(tetrapyran-2-yloxy)-3β-(3α-(tetrahydropyran-2-yloxy)-4-(o-hexylphenoxy)-1(E)-buten-1-yl)-cyclopent-2α-yl)1-6-hexa-3,4-dienoate;

ethyl-(1α-t-butyldimethylsilyloxy-4α-(tetrapyran-2-yloxy)-3β-(3α-(tetrahydropyran-2-yloxy)-4-(m-hexylphenoxy)-1(E)-buten-1-yl)-cyclopent-2α-yl)1-6-hexa-3,4-dienoate;

ethyl-(1α-t-butyldimethylsilyloxy-4α-tetrapyran-2-yloxy)-3β-(3α-(tetrahydropyran-2-yloxy)-4-(m-hexyloxy-phenoxy)-1(E)-buten-1-yl)-cyclopent-2α-yl)-6-hexa-3,4-dienoate;

ethyl-(1α-t-butyldimethylsilyloxy-4α-(tetrapyran-2-yloxy)-3β-(3α-tetrahydropyran-2-yloxy)-4-(o-hexyloxy-phenoxy)-1(E)-buten-1-yl)-cyclopent-2α-yl)-6-hexa-3,4-dienoate; and ethyl-(1α-t-butyldimethylsilyloxy-4α-(tetrapyran-2-yloxy)-3β-(3α-(tetrahydropyran-2-yloxy)-4-(p-hexyloxy-phenoxy)-1(E)-buten-1-yl)-cyclopent-2α-yl)-6-hexa-3,4-dienoate.

EXAMPLE 11

(1α-t-butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)-6-hexa-3,4-dien-1-ol To a three neck reaction flask fitted with a thermometer, pressure equalization addition funnel, dry nitrogen inlet and vacuum outlet was added 62.5 ml of absolute diethyl ether; the reaction system was then purged using dry nitrogen. There was then added, in portions, under a dry nitrogen atmosphere with stirring, 0.32 L g of powdered lithium aluminum hydride. The solution was stirred for 15–20 minutes at ambient temperature and then cooled to about 10° C. A solution of 6.56 g of ethyl-(1α-t-butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)-6-hexa-3,4-dienoate in 23.5 ml of absolute diethyl ether was added at a rate which maintained the temperature between 10°–15° C. The reaction mixture was then stirred at room temperature until the reduction was complete, then again cooled to about 10° C. and 3.0 ml of acetone added over about 15 minutes after which the reaction pot was stirred for an additional 15 minutes. There was then added dropwise 2.5 ml of saturated aqueous potassium tartrate. When there was no more evolution of hydrogen gas, an additional 29.0 ml of saturated aqueous sodium potassium tartrate was added, the reaction pot being at ambient temperature. The aqueous phase was recovered and extracted with 2×25 ml of ethyl acetate. The combined ethereal and ethyl acetate extracts were washed with 35 ml of water. The organic layer was then dried over anhydrous sodium sulfate, filtered and concentrated in vacuo to give the title alcohol having the following $^1$H NMR spectral data:

| δ ppm | |
|---|---|
| 7.28 | 2H, t, J = 7.5 Hz, H-19 |
| 6.86–6.98 | 3H, m, H-18, 20 |
| 5.46–5.83 | 2H, m, H-13-14 |
| 4.96 | m, H-2' THP |
| 4.82 | m, H-2' THP |
| 4.67 | m, H-2' THP |
| 3.88 | 2H, m, H-6' THP |
| 3.47 | 2H, m, H-6' THP |
| 0.89 | 9H, s, t-butyl |
| 0.5 | s, silylmethyl |
| 0.7 | s, silylmethyl |
| 3.9–4.15 | 3H, m, H-11, 16 |
| 4.19 | 1H, m, H-9 |
| 4.52 | 1H, m, H-15 |
| 3.67 | 2H, t, J = 6, H-2 |
| 5.08 | 1H, m, H-4 |
| 5.10 | 1H, m, H-6 |

These same reagents and conditions will reduce any of the dienoate compounds prepared in Example 10 above to the corresponding alcohol.

EXAMPLE 12

(1α-t-butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)-6-(1-methansulfonyloxy)-hexa-3,4-diene To a reaction flask fitted with nitrogen inlet/outlet valves and mechanical stirrer was added 7.24 g of (1α-t-butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)-6-hexa-3,4-dien-1-ol in 67 ml of anhydrous methylene chloride. To this was added 6.7 ml of anhydrous triethylamine at which time the system was purged with dry nitrogen and cooled to about −30° C. There was then added 2.35 g of methanesulfonyl chloride in 13.5 ml of anhydrous methylene chloride over a 15–20 minute period while maintaining the reaction solution at its initial temperature. The reaction mixture was then stirred until the reaction was complete, about 30 minutes. The cooling bath was removed and a solution of 2.0 ml of triethylamine in 20 ml of methylene chloride was added followed by 20 ml of saturated, aqueous sodium bicarbonate. The methylene chloride layer was recovered and the aqueous layer extracted with 2×50 ml of methylene chloride. The combined methylene chloride extracts were washed with 20 ml of saturated sodium bicarbonate-water (1:1-V:V). The organic layer was dried over anhydrous sodium sulfate and solvents removed under reduced pressure to yield the title compound having the following $^1$H NMR spectral data:

| δ ppm | |
|---|---|
| 7.28 | 2H, t, J = 7.5 Hz, H-19 |
| 6.86–6.98 | 3H, m, H-18, 20 |
| 5.46–5.83 | 2H, m, H-13-14 |
| 4.96 | m, H-2' THP |
| 4.81 | m, H-2' THP |
| 4.67 | m, H-2' THP |
| 3.88 | 2H, m, H-6' THP |
| 3.47 | 2H, m, H-6' THP |
| 0.89 | 9H, s, t-butyl |
| 0.5 | s, silylmethyl |
| 0.7 | s, silylmethyl |
| 3.9–4.15 | 3H, m, H-11, 16 |
| 4.19 | 1H, m, H-9 |
| 4.52 | 1H, m, H-15 |
| 4.23 | 2H, t, J = 6, H-2 |
| 5.04 | 1H, m, H-4 |

| δ ppm | |
|---|---|
| 5.13 | 1H, m, H-6 |
| 2.98 | 3H, s, SO₃Me |

Proceeding in this manner, any of the other dienols prepared by the method of Example 11 may be converted to their corresponding mesylates.

EXAMPLE 13

(1α-t-butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)-6-hexa-3,4-dieno-1-nitrile To a flask fitted with dry nitrogen inlet/outlet valves was added 4.7 g of potassium cyanide and 16.5 ml of anhydrous dimethylsulfoxide. This mixture was stirred under dry nitrogen at 75°–80° C. for about 30 minutes. There was then added, in one portion, a solution of 8.13 g of (1α-t-butyldimethylsilyloxy-4α-(tetrahydropyran-2-yloxy)-3β-(3α-(tetrahydropyran-2-yloxy)-4-phenoxy-1(E)-buten-1-yl)-cyclopent-2α-yl)-6-(1-methanesulfonyloxy)-hexa-3,4-diene in 20 ml of anhydrous dimethylsulfoxide. The reaction was continued for about 60 minutes in the 60°–80° C. bath in order to effect completion of the reaction. The reaction solution was then cooled to about 40° C. and 5 ml of methylene chloride added. This mixture was then further cooled to ambient temperature and transferred to a separatory funnel containing 120 ml of methylene chloride. The reaction flask was washed with methylene chloride, the washes being transferred to the extraction funnel. The methylene chloride solution of crude nitrile was shaken with 160 ml of water whereupon the upper aqueous phase was recovered and extracted with 3×40 ml of methylene chloride. The combined methylene chloride extracts were washed with 120 ml of water. The combined aqueous phases were then again extracted with 40 ml of methylene chloride. All methylene chloride extracts were combined and dried over anhydrous sodium sulfate, filtered, and the solvent removed under reduced pressure to yield the captioned compound. The crude nitrile was further purified by passing the crude oil through a silica gel column, eluting with a hexane/50% ethyl acetate-hexane gradient to give fractions of the captioned compound having the following ¹H NMR spectral data:

| δ ppm | |
|---|---|
| 7.28 | 2H, t, J = 7.5 Hz, H-19 |
| 6.86–6.98 | 3H, m, H-18, 20 |
| 5.46–5.83 | 2H, m, H-13–14 |
| 4.96 | m, H-2' THP |
| 4.82 | m, H-2' THP |
| 4.67 | m, H-2' THP |
| 3.88 | 2H, m, H-6' THP |
| 3.47 | 2H, m, H-6' THP |
| 0.89 | 9H, s, t-butyl |
| 0.5 | s, silylmethyl |
| 0.7 | s, silylmethyl |
| 3.9–4.15 | 3H, m, H-11, 16 |
| 4.19 | 1H, m, H-9 |
| 4.52 | 1H, m, H-15 |

The other mesylates, or a similiar sulfonyl ester, prepared in Example 12 may be converted to their corresponding nitrile by the foregoing method as illustrated by the following compounds:

(1α-t-butyldimethylsilyloxy-4α-(tetrapyran-2-yloxy)-3β-(3α-(tetrahydropyran-2-yloxy)-4-(m-trifluoromethylphenoxy)-1(E)-buten-1-yl)-cyclopent-2α-yl)-6-hexa-3,4-dieno-1-nitrile;

(1α-t-butyldimethylsilyloxy-4α-(tetrapyran-2-yloxy)-3β-(3α-(tetrahydropyran-2-yloxy)-4-(m-fluorophenoxy)-1(E)-buten-1-yl)-cyclopent-2α-yl)-6-hexa-3,4-dieno-1-nitrile;

(1α-t-butyldimethylsilyloxy-4α-(tetrapyran-2-yloxy)-3β-(3α-(tetrahydropyran-2-yloxy)-4-(o-fluorophenoxy)-1(E)-buten-1-yl)-cyclopent-2α-yl)-6-hexa-3,4-dieno-1-nitrile;

(1α-t-butyldimethylsilyloxy-4α-(tetrapyran-2-yloxy)-3β-(3α-(tetrahydropyran-2-yloxy)-4-(p-fluorophenoxy)-1(E)-buten-1-yl)-cyclopent-2α-yl)-6-hexa-3,4-dieno-1-nitrile;

(1α-t-butyldimethylsilyloxy-4α-(tetrapyran-2-yloxy)-3β-(3α-(tetrahydropyran-2-yloxy)-4-(p-chlorophenoxy)-1(E)-buten-1-yl)-cyclopent-2α-yl)-6-hexa-3,4-dieno-1-nitrile;

(1α-t-butyldimethylsilyloxy-4α-(tetrapyran-2-yloxy)-3β-(3α-(tetrahydropyran-2-yloxy)-4-(o-chlorophenoxy)-1(E)-buten-1-yl)-cyclopent-2α-yl)-6-hexa-3,4-dieno-1-nitrile;

(1α-t-butyldimethylsilyloxy-4α-(tetrapyran-2-yloxy)-3β-(3α-(tetrahydropyran-2-yloxy)-4-(m-chlorophenoxy)-1(E)-buten-1-yl)-cyclopent-2α-yl)-6-hexa-3,4-dieno-1-nitrile;

(1α-t-butyldimethylsilyloxy-4α-(tetrapyran-2-yloxy)-3β-(3α-(tetrahydropyran-2-yloxy)-4-(m-bromophenoxy)-1(E)-buten-1-yl)-cyclopent-2α-yl)-6-hexa-3,4-dieno-1-nitrile;

(1α-t-butyldimethylsilyloxy-4α-(tetrapyran-2-yloxy)-3β-(3α-(tetrahydropyran-2-yloxy)-4-(o-bromophenoxy)-1(E)-buten-1-yl)-cyclopent-2α-yl)-6-hexa-3,4-dieno-1-nitrile;

(1α-t-butyldimethylsilyloxy-4α-(tetrapyran-2-yloxy)-3β-(3α-(tetrahydropyran-2-yloxy)-4-(p-bromophenoxy)-1(E)-buten-1-yl)-cyclopent-2α-yl)-6-hexa-3,4-dieno-1-nitrile;

(1α-t-butyldimethylsilyloxy-4α-(tetrapyran-2-yloxy)-3β-(3α-(tetrahydropyran-2-yloxy)-4-(p-methylphenoxy)-1(E)-buten-1-yl)-cyclopent-2α-yl)-6-hexa-3,4-dieno-1-nitrile;

(1α-t-butyldimethylsilyloxy-4α-(tetrapyran-2-yloxy)-3β-(3α-(tetrahydropyran-2-yloxy)-4-(o-methylphenoxy)-1(E)-buten-1-yl)-cyclopent-2α-yl)-6-hexa-3,4-dieno-1-nitrile;

(1α-t-butyldimethylsilyloxy-4α-(tetrapyran-2-yloxy)-3β-(3α-(tetrahydropyran-2-yloxy)-4-(m-methylphenoxy)-1(E)-buten-1-yl)-cyclopent-2α-yl)-6-hexa-3,4-dieno-1-nitrile;

(1α-t-butyldimethylsilyloxy-4α-(tetrapyran-2-yloxy)-3β-(3α-(tetrahydropyran-2-yloxy)-4-(m-methoxyphenoxy)-1(E)-buten-1-yl)-cyclopent-2α-yl)-6-hexa-3,4-dieno-1-nitrile;

(1α-t-butyldimethylsilyloxy-4α-(tetrapyran-2-yloxy)-3β-(3α-(tetrahydropyran-2-yloxy)-4-(o-methoxyphenoxy)-1(E)-buten-1-yl)-cyclopent-2α-yl)-6-hexa-3,4-dieno-1-nitrile;

(1α-t-butyldimethylsilyloxy-4α-(tetrapyran-2-yloxy)-3β-(3α-(tetrahydropyran-2-yloxy)-4-(p-methoxyphenoxy)-1(E)-buten-1-yl)-cyclopent-2α-yl)-6-hexa-3,4-dieno-1-nitrile;

(1α-t-butyldimethylsilyloxy-4α-(tetrapyran-2-yloxy)-3β-(3α-(tetrahydropyran-2-yloxy)-4-(p-hexylphenoxy)-1(E)-buten-1-yl)-cyclopent-2α-yl)-6-hexa-3,4-dieno-1-nitrile;

(1α-t-butyldimethylsilyloxy-4α-(tetrapyran-2-yloxy)-
3β-(3α-(tetrahydropyran-2-yloxy)-4-(o-hexylphenoxy)-1(E)-buten-1-yl)-cyclopent-2α-yl)-B    6-hexa-3,4-dieno-1-nitrile;

(1α-t-butyldimethylsilyloxy-4α-(tetrapyran-2-yloxy)-
3β-(3α-(tetrahydropyran-2-yloxy)-4-(m-hexylphenoxy)-1(E)-buten-1-yl)-cyclopent-2α-yl)-6-hexa-3,4-dieno-1-nitrile;

(1α-t-butyldimethylsilyloxy-4α-(tetrapyran-2-yloxy)-
3β-(3α-(tetrahydropyran-2-yloxy)-4-(m-hexyloxyphenoxy)-1(E)-buten-1-yl)-cyclopent-2α-yl)-6-hexa-3,4-dieno-1-nitrile;

(1α-t-butyldimethylsilyloxy-4α-(tetrapyran-2-yloxy)-
3β-(3α-tetrahydropyran-2-yloxy)-4-(o-hexyloxyphenoxy)-1(E)-buten-1-yl)-cyclopent-2α-yl)-6-hexa-3,4-dieno-1-nitrile; and (1α-t-butyldimethylsilyloxy-4α-(tetrapyran-2-yloxy)-
3β-(3α-(tetrahydropyran-2-yloxy)-4-(p-hexyloxyphenoxy)-1(E)-buten-1-yl)-cyclopent-2α-yl)-6-hexa-3,4-dieno-1-nitrile.

EXAMPLE 14

Methyl
9α-hydroxy-11α,15α-bis-(tetrahydropyran-2-yloxy)-16-phenoxy-17,18,19,20-tetranorprosta-4,5,13(E)-trienoate A reaction flask fitted with a condenser and nitrogen inlet/outlet valves was charged with 3.47 g of the 1-nitrile from Example 13 dissolved in 37.0 ml of 2-methoxyethanol. To this was added a solution of 0.9 g of potassium hydroxide in 3.1 ml of water after which the system was vacuum purged with dry nitrogen. The reaction was then heated at reflux under nitrogen for approximately 63 hours. The reaction mixture was then cooled to about 50°–60° C. and the solvents removed under reduced pressure. The residue was dissolved in 5.0 ml of water and transferred to a reaction flask equipped with a pressure equalization addition funnel and pH electrode. The solution was cooled to between 5°–10° C. and cool (10° C.) aqueous hydrochloric acid (1 part conc. HCl to 2 parts water) was added until the pH of the solution was approximately 2. Ethyl acetate/diethyl ether (1:1), 20 ml, was added and the system stirred at ambient temperature. The aqueous phase was recovered and extracted with additional 2×20 ml aliquots of ethyl acetate/diethyl ether (1:1). The combined organic layers were washed with 2×5 ml of water, dried over anhydrous sodium sulfate and filtered. Solvent was removed under reduced pressure to yield a crude residue of the title acid.

At this point the acid may be recovered and purified by conventional means such as by extraction, chromatography and the like. The acid has the following $^1$H NMR spectral data:

| δ ppm | |
|---|---|
| 7.28 | 2H, t, J = 7.5 Hz, H-19 |
| 6.86–6.98 | 3H, m, H-18, 20 |
| 5.46–5.87 | 2H, m, H-13–14 |
| 4.95 | m, H-2' THP |
| 4.85 | m, H-2' THP |
| 4.67 | m, H-2' THP |
| 3.88 | 2H, m, H-6' THP |
| 3.47 | 2H, m, H-6' THP |
| 3.9–4.15 | 3H, m, H-11, 16 |
| 4.19 | 1H, m, H-9 |
| 4.52 | 1H, m, H-15 |

Alternatively, however, without further purification the crude acid was transferred to a reaction flask in 45 ml of dimethylformamide. To this solution was added 1.65 g of powdered sodium bicarbonate followed by 2.9 ml of methyl iodide.

This solution was stirred at 45° C. for 48 hours or until esterification was completed. The reaction mixture was filtered through celite. The filter cake was washed with 50 ml of methylene chloride and the combined organic solvents were evaporated under reduced pressure to afford an oily residue. This residue was taken up in 65 ml of methylene chloride which was washed with 2×15 ml of water. The aqueous layer was back-extracted with methylene chloride which was combined with the other methylene chloride solution, dried over anhydrous sodium sulfate and filtered. Removal of the solvent afforded a crude methyl ester which was further purified chromatographically on silica gel. Chromatographic purification was effected using a hexane/50% ethyl acetate-hexane gradient, 75% ethyl acetate-hexane and finally ethyl acetate, as needed. Fractions containing the pure methyl ester were combined and the solvent removed under reduced pressure to give the title compound having the following $^1$H NMR spectral data:

| δ ppm | |
|---|---|
| 7.28 | 2H, t, J = 7.5 Hz, H-19 |
| 6.86–6.98 | 3H, m, H-18, 20 |
| 5.46–5.83 | 2H, m, H-13–14 |
| 4.96 | m, H-2' THP |
| 4.79 | m, H-2' THP |
| 4.70 | m, H-2' THP |
| 3.88 | 2H, m, H-6' THP |
| 3.47 | 2H, m, H-6' THP |
| 3.9–4.15 | 3H, m, H-11, 16 |
| 4.23 | 1H, m, H-9 |
| 4.52 | 1H, m, H-15 |
| 3.67 | 3H, s, OMe |

This procedure will also serve to convert the other nitrile compounds prepared in Example 13 to their corresponding 9-hydroxy-dienoic methyl esters, illustrated by the following compounds:

methyl 9α-hydroxy-11α,15α-bis-(tetrapyran-2-yloxy)-16-m-trifluoromethylphenoxy-17,18,19,20-tetranorprosta-4,5,13(E)trienoate;

methyl 9α-hydroxy-11α,15α-bis-(tetrapyran-2-yloxy)-16-m-fluorophenoxy-17,18,19,20-tetranorprosta-4,5,13(E)-trienoate;

methyl 9α-hydroxy-11α,15α-bis-(tetrapyran-2-yloxy)-16-o-fluorophenoxy-17,18,19,20-tetranorprosta-4,5,13(E)-trienoate;

methyl 9α-hydroxy-11α,15α-bis-(tetrapyran-2-yloxy)-16-p-fluorophenoxy-17,18,19,20-tetranorprosta-4,5,13(E)-trienoate;

methyl 9α-hydroxy-11α,15α-bis-(tetrapyran-2-yloxy)-16-p-chlorophenoxy-17,18,19,20-tetranorprosta-4,5,13(E)-trienoate;

methyl 9α-hydroxy-11α,15α-bis-(tetrapyran-2-yloxy)-16-o-chlorophenoxy-17,18,19,20-tetranorprosta-4,5,13(E)-trienoate;

methyl 9α-hydroxy-11α,15α-bis-(tetrapyran-2-yloxy)-16-m-chlorophenoxy-17,18,19,20-tetranorprosta-4,5,13(E)-trienoate;

methyl 9α-hydroxy-11α,15α-bis-(tetrapyran-2-yloxy)-16-m-bromophenoxy-17,18,19,20-tetranorprosta-4,5,13(E)-trienoate;

methyl 9α-hydroxy-11α,15α-bis-(tetrapyran-2-yloxy)-16-o-bromophenoxy-17,18,19,20-tetranorprosta-4,5,13(E)-trienoate;

methyl 9α-hydroxy-11α,15α-bis-(tetrapyran-2-yloxy)-16-p-bromophenoxy-17,18,19,20-tetranorprosta-4,5,13(E)-trienoate;

methyl 9α-hydroxy-11α,15α-bis-(tetrapyran-2-yloxy)-16-p-methylphenoxy-17,18,19,20-tetranorprosta-4,5,13(E)-trienoate;

methyl 9α-hydroxy-11α,15α-bis-(tetrapyran-2-yloxy)-16-o-methylphenoxy-17,18,19,20-tetranorprosta-4,5,13(E)-trienoate;

methyl 9α-hydroxy-11α,15α-bis-(tetrapyran-2-yloxy)-16-m-methylphenoxy-17,18,19,20-tetranorprosta-4,5,13(E)-trienoate;

methyl 9α-hydroxy-11α,15α-bis-(tetrapyran-2-yloxy)-16-m-methoxyphenoxy-17,18,19,20-tetranorprosta-4,5,13(E)-trienoate;

methyl 9α-hydroxy-11α,15α-bis-(tetrapyran-2-yloxy)-16-o-methoxyphenoxy-17,18,19,20-tetranorprosta-4,5,13(E)-trienoate;

methyl 9α-hydroxy-11α,15α-bis-(tetrapyran-2-yloxy)-16-p-methoxyphenoxy-17,18,19,20-tetranorprosta-4,5,13(E)-trienoate;

methyl 9α-hydroxy-11α,15α-bis-(tetrapyran-2-yloxy)-16-p-hexylphenoxy-7,18,19,20-tetranorprosta-4,5,13(E)-trienoate;

methyl 9α-hydroxy-11α,15α-bis-(tetrapyran-2-yloxy)-16-o-hexylphenoxy-17,18,19,20-tetranorprosta-4,5,13(E)-trienoate;

methyl 9α-hydroxy-11α,15α-bis-(tetrapyran-2-yloxy)-16-m-hexylphenoxy-17,18,19,20-tetranorprosta-4,5,13(E)-trienoate;

methyl 9α-hydroxy-11α,15α-bis-(tetrapyran-2-yloxy)-16-m-hexyloxyphenoxy-17,18,19,20-tetranorprosta-1(E)-buten-1-yl)-cyclopent-2α-yl)-6-hexa-3,4-dieno-1-nitrile;

methyl 9α-hydroxy-11α,15α-bis-(tetrapyran-2-yloxy)-16-o-hexyloxyphenoxy-17,18,19,20-tetraorprosta-4,5,13(E)-trienoate;

methyl 9α-hydroxy-11α,15α-bis-(tetrapyran-2-yloxy)-16-p-hexyloxyphenoxy-17,18,19,20-tetranorprosta-4,5,13(e)-trienoate;

9α-hydroxy-11α,15α-bis-(tetrahydropyran-2-yloxy)-16-phenoxy-17,18,19,20-tetranorprosta-4,5,13(E)-trienoic acid;

9α-hydroxy-11α,15α-bis-(tetrahydropyran-2-yloxy)-16-o-fluorophenoxy-17,18,19,20-tetranorprosta-4,5,13(E)-trienoic acid;

9α-hydroxy-11α,15α-bis-(tetrahydropyran-2-yloxy)-16-p-fluorophenoxy-17,18,19,20-tetranorprosta-4,5,13(E)-trienoic acid;

9α-hydroxy-11α,15α-bis-(tetrahydropyran-2-yloxy)-16-m-fluorophenoxy-17,18,19,20-tetranorprosta-4,5,13(E)-trienoic acid;

9α-hydroxy-11α,15α-bis-(tetrahydropyran-2-yloxy)-16-m-methylphenoxy-17,18,19,20-tetranorprosta-4,5,13(E)-trienoic acid;

9α-hydroxy-11α,15α-bis-(tetrahydropyran-2-yloxy)-16-p-methylphenoxy-17,18,19,20-tetranorprosta-4,5,13(E)-trienoic acid;

9α-hydroxy-11α,15α-bis-(tetrahydropyran-2-yloxy)-16-p-methoxyphenoxy-17,18,19,20-tetranorprosta-4,5,13(E)-trienoic acid;

9α-hydroxy-11α,15α-bis-(tetrahydropyran-2-yloxy)-16-o-methoxyphenoxy-17,18,19,20-tetranorprosta-4,5,13(E)-trienoic acid; and 9α-hydroxy-11α,15α-bis-(tetrahydropyran-2-yloxy)-16-p-methoxyphenoxy-17,18,19,20-tetranorprosta-4,5,13(E)-trienoic acid.

EXAMPLE 15

Methyl 9α-oxo-11α,15α-bis-(tetrahydropyran-2-yloxy)-16-phenoxy-17,18,19,20-tetranorprosta-4,5,13(E)-trienoate To a suspension of chromium trioxide (2.66 g) in methylene chloride (100 ml) cooled to about −20° C. was added solid 3,5-dimethylpyrazole (2.58 g) under dry nitrogen. After stirring for approximately ½ hour at −20° C., 3.37 g of methyl 9α-hydroxy-11α,15α-bis(tetrahydropyran-2-yloxy)-16-phenoxy-17,18,19,20-tetranorprosta-4,5,13(E)-trienoate dissolved in 50 ml of methylene chloride was added. Stirring was continued at the reduced temperature for approximately 1 hour. Silica gel (50 g) was then added and the solvent removed under reduced pressure. The impregnated silica gel was charged onto the top of a silica gel column made up in hexane. Recovery and separation of the title compound was effected by a 5%–50% gradient of ethyl acetate in hexane. Combined appropriate fractions were concentrated under reduced pressure to give the title compound having the following $^1$H NMR spectral data:

| δ ppm | |
|---|---|
| 7.28 | 2H, t, J = 7.5 Hz, H-19 |
| 6.86–6.98 | 3H, m, H-18, 20 |
| 5.48–5.95 | 2H, m, H-13–14 |
| 4.96 | m, H-2' THP |
| 4.82 | m, H-2' THP |
| 4.67 | m, H-2' THP |
| 3.88 | 2H, m, H-6' THP |
| 3.50 | 2H, m, H-6' THP |
| 3.9–4.15 | 3H, m, H-11, 16 |
| 4.19 | 1H, m, H-9 |
| 4.56 | 1H, m, H-15 |
| 3.66 | 3H, s, OMe |

Proceeding in a similar manner, but substituting the appropriate methyl ester or free acid prepared in Example 14 for the 16-phenoxy-substituted compound herein above, all compounds prepared in Example 14 are converted to their corresponding C-9 oxo compound as illustrated by the following compounds:

methyl 9-oxo-11α,15α-bis(tetrapyran-2-yloxy)-16-m-trifluoromethylphenoxy-17,18,19,20-tetranorprosta-4,5,13(E)-trienoate;

methyl 9-oxo-11α,15α-bis-(tetrapyran-2-yloxy)-16-m-fluorophenoxy-17,18,19,20-tetranorprosta-4,5,13(E)-trienoate;

methyl 9-oxo-11α,15α-bis-(tetrapyran-2-yloxy)-16-o-fluorophenoxy-17,18,19,20-tetranorprosta-4,5,13(E)-trienoate;

methyl 9-oxo-11α,15α-bis-(tetrapyran-2-yloxy)-16-p-fluorophenoxy-17,18,19,20-tetranorprosta-4,5,13(E)-trienoate;

methyl 9-oxo-11α,15α-bis-(tetrapyran-2-yloxy)-16-p-chlorophenoxy-17,18,19,20-tetranorprosta-4,5,13(E)-trienoate;

methyl 9-oxo-11α,15α-bis-(tetrapyran-2-yloxy)-16-o-chlorophenoxy-17,18,19,20-tetranorprosta-4,5,13(E)-trienoate;

methyl 9-oxo-11α,15α-bis-(tetrapyran-2-yloxy)-16-m-chlorophenoxy-17,18,19,20-tetranorprosta-4,5,13(E)-trienoate;

methyl 9-oxo-11α,15α-bis-(tetrapyran-2-yloxy)-16-m-bromophenoxy-17,18,19,20-tetranorprosta-4,5,13(E)-trienoate;

methyl 9-oxo-11α,15α-bis-(tetrapyran-2-yloxy)-16-o-bromophenoxy-17,18,19,20-tetranorprosta-4,5,13(E)-trienoate;

methyl 9-oxo-11α,15α-bis-(tetrapyran-2-yloxy)-16-p-bromophenoxy-17,18,19,20-tetranorprosta-4,5,13(E)-trienoate;

methyl 9-oxo-11α,15α-bis-(tetrapyran-2-yloxy)-16-p-methylphenoxy-7,18,19,20-tetranorprosta-4,5,13(E)-trienoate;

methyl 9-oxo-11α,15α-bis-(tetrapyran-2-yloxy)-16-o-methylphenoxy-17,18,19,20-tetranorprosta-4,5,13(E)-trienoate;

methyl 9-oxo-11α,15α-bis-(tetrapyran-2-yloxy)-16-m-methylphenoxy-17,18,19,20-tetranorprosta-4,5,13(E)-trienoate;

methyl 9-oxo-11α,15α-bis-(tetrapyran-2-yloxy)-16-m-methoxyphenoxy-17,18,19,20-tetranorprosta-4,5,13(E)-trienoate;

methyl 9-oxo-11α,15α-bis-(tetrapyran-2-yloxy)-16-o-methoxyphenoxy-17,18,19,20-tetranorprosta-4,5,13(E)-trienoate;

methyl 9-oxo-11α,15α-bis-(tetrapyran-2-yloxy)-16-p-methoxyphenoxy-17,18,19,20-tetranorprosta-4,5,13(E)-trienoate;

methyl 9-oxo-11α,15α-bis-(tetrapyran-2-yloxy)-16-p-hexylphenoxy-17,18,19,20-tetranorprosta-4,5,13(E)-trienoate;

methyl 9-oxo-11α,15α-bis-(tetrapyran-2-yloxy)-16-o-hexylphenoxy-17,18,19,20-tetranorprosta-4,5,13(E)-trienoate;

methyl 9-oxo-11α,15α-bis-(tetrapyran-2-yloxy)-16-m-hexylphenoxy-17,18,19,20-tetranorprosta-4,5,13(E)-trienoate;

methyl 9-oxo-11α,15α-bis-(tetrapyran-2-yloxy)-16-m-hexyloxyphenoxy-17,18,19,20-tetranorprosta-4,5,13(E)-trienoate;

methyl 9-oxo-11α,15α-bis-(tetrapyran-2-yloxy)-16-o-hexyloxyphenoxy-17,18,19,20-tetranorprosta-4,5,13(E)-trienoate;

methyl 9-oxo-11α,15α-bis-(tetrapyran-2-yloxy)-16-p-hexyloxyphenoxy-17,18,19,20-tetranorprosta-4,5,13(e)-trienoate;

9-oxo-11α,15α-bis-(tetrahydropyran-2-yloxy)-16-phenoxy-17,18,19,20-tetranorprosta-4,5,13(E)-trienoate;

9-oxo-11α,15α-bis-(tetrahydropyran-2-yloxy)-16-o-fluorophenoxy-17,18,19,20-tetranorprosta-4,5,13(E)-trienoate;

9-oxo-11α,15α-bis-(tetrahydropyran-2-yloxy)-16-p-fluorophenoxy-17,18,19,20-tetranorprosta-4,5,13(E)-trienoate;

9-oxo-11α,15α-bis-(tetrahydropyran-2-yloxy)-16-m-fluorophenoxy-17,18,19,20-tetranorprosta-4,5,13(E)-trienoate;

9-oxo-11α,15α-bis-(tetrahydropyran-2-yloxy)-16-m-methylphenoxy-17,18,19,20-tetranorprosta-4,5,13(E)-trienoate;

9-oxo-11α,15α-bis-(tetrahydropyran-2-yloxy)-16-p-methoxyphenoxy-17,18,19,20-tetranorprosta-4,5,13(E)-trienoate;

9-oxo-11α,15α-bis-(tetrahydropyran-2-yloxy)-16-p-methoxyphenoxy-17,18,19,20-tetranorprosta-4,5,13(E)-trienoate;

9-oxo-11α,15α-bis-(tetrahydropyran-2-yloxy)-16-o-methoxyphenoxy-17,18,19,20-tetranorprosta-4,5,13(E)-trienoate; and 9-oxo-11α,15α-bis-(tetrahydropyran-2-yloxy)-16-p-methoxyphenoxy-17,18,19,20-tetranorprosta-4,5,13(E)-trienoate.

EXAMPLE 16

Methyl-9-oxo-11α,15α-bis-(tetrahydropyran-2-yloxy)-16-phenoxy-17,18,19,20-tetranorprosta-4,5,13(E)-trienoate A 0.3 mg aliquot of 9-oxo-11α,15α-bis-(tetrahydropyran-2-yloxy)-16-phenoxy-17,18,19,20-tetranorprosta-4,5,13(E)-trienoic acid was dissolved in 10 ml of anhydrous diethyl ether to which was added an excess of diazomethane at room temperature. The reaction was followed by tlc and when complete, the ether and excess diazomethane was removed under vacuum to give the title methyl ester.

Proceeding in the same manner, all the 9-oxo acid compounds prepared in Example 15 are converted to their corresponding methyl ester as illustrated by the following compounds:

methyl 9-oxo-11α,15α-bis-(tetrapyran-2-yloxy)-16-m-trifluoromethylphenoxy-17,18,19,20-tetranorprosta-4,5,13(E)trienoate;

methyl 9-oxo-11α,15α-bis-(tetrapyran-2-yloxy)-16-m-fluorophenoxy-17,18,19,20-tetranorprosta-4,5,13(E)-trienoate;

methyl 9-oxo-11α,15α-bis-(tetrapyran-2-yloxy)-16-o-fluorophenoxy-17,18,19,20-tetranorprosta-4,5,13(E)-trienoate;

methyl 9-oxo-11α,15α-bis-(tetrapyran-2-yloxy)-16-p-fluorophenoxy-17,18,19,20-tetranorprosta-4,5,13(E)-trienoate;

methyl 9-oxo-11α,15α-bis-(tetrapyran-2-yloxy)-16-p-chlorophenoxy-17,18,19,20-tetranorprosta-4,5,13(E)-trienoate;

methyl 9-oxo-11α,15α-bis-(tetrapyran-2-yloxy)-16-o-chlorophenoxy-17,18,19,20-tetranorprosta-4,5,13(E)-trienoate;

methyl 9-oxo-11α,15α-bis-(tetrapyran-2-yloxy)-16-m-chlorophenoxy-17,18,19,20-tetranorprosta-4,5,13(E)-trienoate;

methyl-9-oxo-11α,15α-bis-(tetrapyran-2-yloxy)-16-m-bromophenoxy-17,18,19,20-tetranorprosta-4,5,13(E)-trienoate;

methyl 9-oxo-11α,15α-bis-(tetrapyran-2-yloxy)-16-o-bromophenoxy-17,18,19,20-tetranorprosta-4,5,13(E)-trienoate;

methyl 9-oxo-11α,15α-bis-(tetrapyran-2-yloxy)-16-p-bromophenoxy-17,18,19,20-tetranorprosta-4,5,13(E)-trienoate;

methyl 9-oxo-11α,15α-bis-(tetrapyran-2-yloxy)-16-p-methylphenoxy-17,18,19,20-tetranorprosta-4,5,13(E)-trienoate;

methyl 9-oxo-11α,15α-bis-(tetrapyran-2-yloxy)-16-o-methylphenoxy-17,18,19,20-tetraorprosta-4,5,13(E)-trienoate;

methyl 9-oxo-11α,15α-bis-(tetrapyran-2-yloxy)-16-m-methylphenoxy-17,18,19,20-tetranorprosta-4,5,13(E)-trienoate;

methyl 9-oxo-11α,15α-bis-(tetrapyran-2-yloxy)-16-m-methoxyphenoxy-17,18,19,20-tetranorprosta-4,5,13(E)-trienoate;

methyl 9-oxo-11α,15α-bis-(tetrapyran-2-yloxy)-16-o-methoxyphenoxy-17,18,19,20-tetranorprosta-4,5,13(E)-trienoate; and methyl 9-oxo-11α,15α-bis-(tetrapyran-2-yloxy)-16-p-methoxyphenoxy-17,18,19,20-tetranorprosta-4,5,13(E)-trienoate.

EXAMPLE 17

Methyl 9-oxo-11α,15α-dihydroxy-16-phenoxy-17,18,19,20-tetranorprosta-4,5,13(E)-trienoate A 0.3 mg aliquot of the protected methyl ester of Example 15 was dissolved in a solution of glacial acetic acid (10.0 ml), water (6.0 ml) and tetrahydrofuran (1.7 ml). This reaction mixture was stirred for 12 hours at about 40° C. under dry nitrogen. The solvents were removed under reduced pressure. The resulting residue was subjected to azeotropic distillation with toluene (3×10 ml). Further purification was effected on a silica gel column made up in hexane, the product being eluted with 75% ethyl acetate in hexane. Appropriate fractions were combined and evaporated to dryness under reduced pressure to give the title compound.

Proceeding in a similar manner, the esters prepared in Examples 15 and 16 are converted to their corresponding dihydroxy compound as illustrated by the following compounds:

methyl 9-oxo-11α,15α-dihydroxy-16-m-trifluoromethylphenoxy-17,18,19,20-tetranorprosta-4,5,13(E)-trienoate;

methyl 9-oxo-11α,15α-dihydroxy16-m-fluorophenoxy-17,18,19,20-tetranorprosta-4,5,13(E)-trienoate;

methyl 9-oxo-11α,15α-dihydroxy-16-o-fluorophenoxy-17,18,19,20-tetranorprosta-4,5,13(E)-trienoate;

methyl 9-oxo-11α,15α-dihydroxy-16-p-fluorophenoxy-17,18,19,20-tetranorprosta-4,5,13(E)-trienoate;

methyl 9-oxo-11α,15α-dihydroxy-16-p-chlorophenoxy-17,18,20-tetranorprosta-4,5,13(E)-trienoate;

methyl 9-oxo-11α,15α-dihydroxy-16-o-chlorophenoxy-17,18,19,20-tetranorprosta-4,5,13(E)-trienoate;

methyl 9-oxo-11α,15α-dihydroxy-16-m-chlorophenoxy-17,18,19,20-tetranorprosta-4,5,13(E)-trienoate;

methyl 9-oxo-11α,15α-dihydroxy-16-m-bromophenoxy-17,18,19,20-tetranorprosta-4,5,13(E)-trienoate;

methyl 9-oxo-11α,15α-dihydroxy-16-o-bromophenoxy-17,18,19,20-tetranorprosta-4,5,13(E)-trienoate;

methyl 9-oxo-11α,15α-dihydroxy-16-p-bromophenoxy-17,18,19,20-tetranorprosta-4,5,13(E)-trienoate;

methyl 9-oxo-11α,15α-dihydroxy-16-p-methylphenoxy-17,18,19,20-tetranorprosta-4,5,13(E)-trienoate;

methyl 9-oxo-11α,15α-dihydroxy-16-o-methylphenoxy-17,18,19,20-tetranorprosta-4,5,13(E)-trienoate;

methyl 9-oxo-11α,15α-dihydroxy-16m-methylphenoxy-17,18,19,20-tetranorprosta-4,5,13(E)-trienoate;

methyl 9-oxo-11α,15α-dihydroxy-16-m-methoxyphenoxy-17,18,19,20-tetranorprosta-4,5,13(E)-trienoate;

methyl 9-oxo-11α,15α-dihydroxy-16-o-methoxyphenoxy-17,18,19,20-tetranorprosta-4,5,13(E)-trienoate;

methyl 9-oxo-11α,15α-dihydroxy-16-p-methoxyphenoxy-17,18,19,20-tetranorprosta-4,5,13(E)-trienoate;

methyl 9-oxo-11α,15α-dihydroxy-16-p-hexylphenoxy-17,18,19,20-tetranorprosta-4,5,13(E)-trienoate;

methyl 9-oxo-11α,15α-dihydroxy-16-o-hexylphenoxy-17,18,9,20-tetranorprosta-4,5,13(E)-trienoate;

methyl 9-oxo-11α,15α-dihydroxy-16-m-hexylphenoxy-17,18,19,20-tetranorprosta-4,5,13(E)-trienoate;

methyl 9-oxo-11α,15α-dihydroxy-16-m-hexyloxyphenoxy-17,18,19,20-tetranorprosta-4,5,13(E)-trienoate;

methyl 9-oxo-11α,15α-dihydroxy)-16-o-hexyloxyphenoxy-17,18,19,20-tetranorprosta-4,5,13(E)-trienoate; and methyl 9-oxo-11α,15α-dihydroxy)-16-p-hexyloxyphenoxy-17,18,19,20-tetranorprosta-4,5,13(E)-trienoate.

This procedure may also be used to hydrolytically cleave the ether groups of any of the intermediates set out herein in the foregoing Examples.

EXAMPLE 18

Methyl 9-oxo-11α,15α-dihydroxy-16-phenoxy-17,18,19,20-tetranorprosta-4,5,13(E)-trienoate A 500 mg aliquot of the protected methyl ester prepared in Example 15 was dissolved in methylene chloride and 0.1 ml of 48% hydrofluoric acid added with vigorous stirring. There was then added dropwise, 7.5 ml of a methylene chloride solution of mercaptoethanol (17 mg/ml) over 30 minutes. The solution was then neutralized with approximately 0.3 ml of aqueous sodium bicarbonate. Methylene chloride was used to extract the product. The combined extracts were dried with sodium sulfate, the solvent removed uner reduced pressure and the product purified using a silica gel column. The column was eluted in steps with 20% ethyl acetate/hexane, 50% and 75% ethyl acetate/hexane and finally ethyl acetate. As in Example 17, all alkyl ester compounds prepared in Examples 15 and 16 may be hydrolyzed by the foregoing procedure.

Individual alkyl 9-oxo-11α,15α-dihydroxy-16-phenoxy-trienoate isomers were prepared by taking a single propargyl alcohol isomer as prepared in Example 9 and carrying that single isomer through the subsequent steps as set out in Examples 10–18

As in Example 9, $^{13}C$ NMR spectra were measured on a mixture and on the individual allene isomers. The spectra were obtained in the same manner and under the same conditions as set out in Example 9 except that $CD_3OD$ was not added to solubilize the compound in $CDCl_3$. The spectral data here are numbered the same as in Example 9. The allenic isomer designated "R" here was derived from isomer "1" of Example 9 and the allenic isomer "S" was derived from isomer "2" of Example. The spectral data are as follows:

| MIXTURE OF ISOMERS | | |
|---|---|---|
| 1. 173.59 | 6. 88.76 | 11. 71.97, 72.01 |
| 2. 33.08, 33.24 | 7. 26.73 | 12. 54.14, 54.19 |
| 3. 23.71, 23.83 | 8. 53.34, 53.48 | 13. 131.91 |
| 4. 90.26, 90.40 | 9. 213.63, 213.40 | 14. 133.23, 133.34 |
| 5. 204.79 | 10. 45.99 | 15. 70.80 |
| 16. 71.57 | | |
| 17. 158.39 | | |
| 18. 114.65 | | |
| 19. 129.64 | | |
| 20. 121.43 | | |
| OMe 51.65 | | |
| 1. 173.58 | 6. 88.77 | 11. 71.94 |
| 2. 33.08 | 7. 26.70 | 12. 54.13 |
| 3. 23.70 | 8. 53.43 | 13. 131.90 |
| 4. 90.37 | 9. 213.62 | 14. 133.49 |

-continued

| | | |
|---|---|---|
| 5. 204.75 | 10. 45.94 | 15. 70.86 |
| 16. 71.54 | | |
| 17. 158.39 | | |
| 18. 114.63 | | |
| 19. 129.62 | | |
| 20. 121.40 | | |
| Ome 51.63 | | |

THE "S" ALLENIC ISOMER

| | | |
|---|---|---|
| 1. 173.53 | 6. 88.74 | 11. 71.98 |
| 2. 33.24 | 7. 26.75 | 12. 54.19 |
| 3. 23.83 | 8. 53.46 | 13. 131.91 |
| 4. 90.26 | 9. 213.62 | 14. 133.23 |
| 5. 204.71 | 10. 46.02 | 15. 70.79 |
| 16. 71.58 | | |
| 17. 158.39 | | |
| 18. 114.65 | | |
| 19. 129.63 | | |
| 20. 121.42 | | |
| OMe 51.65 | | |

EXAMPLE 19

Crystalline (4,5,6R,8R)methyl 9-oxo-11α,15α-dihydroxy-16-phenoxy-17,18,19,20-tetranorprosta-4,5,13(E)-trienoate Approximately 720 mg of (4,5,6R,8R)-methyl 9-oxo-11α,15α-dihydroxy-16-phenoxy-17,18,19,20-tetranorprosta-4,5,13(E)-trienoate as an oil was stored in a freezer where the oily material spontaneously crystallized. A sample (50 mg) of the solid material was purified by flash chromatography, then crystallized from ethyl acetate/hexane to give needle shaped crystals with a melting point of 71°–71.5° C. The material was determined 98% pure by HPLC.

EXAMPLE 20

Biological activity of (4,5,6R,8R) methyl 9-oxo-11α,15α-dihydroxy-16-phenoxy-17,18,19,20-tetranorprosta-4,5,13(E)-trienoate (Histamine Induced Gastric Acid Secretion Assay)

Spraque-Dawley (Hilltop) male rats were used in the assay. Animals had a circular plastic collar fastened around their necks in order to prevent access to food or feces and assure gastric emptying during a 48 hour starvation period. The title compound was administered orally by gavage during the morning of the experiment, 30 minutes prior to surgery. During this procedure animals were ether anesthetized and one ligature was placed on the duodenum adjacent to the pyloric sphincter and another or the esophagus posterior to the larynx. The laparotomy was closed with wound clips and 40 mg/kg histamine diphosphate was injected once subcutaneously during a 3 hour study interval of stimulated gastric acid secretion. At the end of the 3 hours rats were sacrificed, gastric juice content of the stomach aspirated, and its volume recorded. An aliquot of the juice was titrated with 0.02N NaOH to pH=7.0±0.1 end point on a pH meter. Gastric acid secreted was calculated as milli-equivalents per 100 g body weight. Treated groups were compared statistically to control. In this test, (4,5,6R,8R)methyl 9-oxo-11α,15α-dihydroxy-16-phenoxy-17,18,19,20-tetranorprosta-4,5,13(E)-trienoate, given at doses of from 0.5 to 4 μg/kg, was found to have an extrapolated ED$_{50}$ of 6 μg/kg.

EXAMPLE 21

Toxicity of (4,5,6R,8R)methyl 9-oxo-11α,15α-dihydroxy-16-phenoxy-17,18,19,20-tetranorprosta-4,5,13(E)-trienoate (4,5,6R,8R)methyl 9-oxo-11α,15α-dihydroxy-16-phenoxy-17,18,19,20-tetranorprosta-4,5,13(E)-trienoate was given to male (Sim (ICR) FBR) mice intraperitoneally at doses from 0.125–0.5 mg/Kg. No deaths were noted at the doses given.

What is claimed is:

1. A process for preparing a compound of the formula

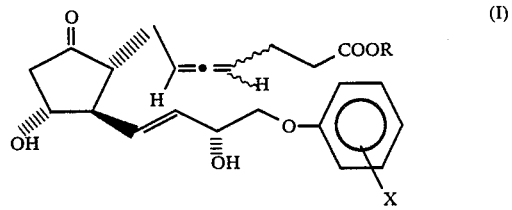

(I)

or its counterpart of the unnatural prostaglandin configuration, or mixtures thereof, wherein R is hydrogen or a lower alkyl, preferably methyl; X is hydrogen, halo, trifluoromethyl, lower alkyl or lower alkoxy, preferably hydrogen, and the wavy lines represent the α or β configuration with the proviso that when one wavy line is α the other is β, or a pharmaceutically acceptable, non-toxic salt of the compound of formula I wherein R is hydrogen, which process comprises hydrolyzing with acid the $R^1$ groups of a compound of the formula

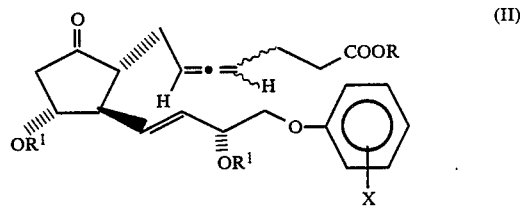

(II)

or its counterpart of the unnatural prostaglandin configuration, or mixtures thereof, wherein R, X and the wavy lines are as defined above and $R^1$ is a base-stabile acid-labile ether-forming group, preferably tetrahydropyranyl, tetrahydrofuranyl or 2-ethoxyethyl most preferably tetrahydropyranyl, and optionally converting the compound of formula I wherein R is hydrogen to its pharmaceutically acceptable, non-toxic salts.

2. The process of claim 1 wherein said acid is an alkanoic acid of 1 to 6 carbons, preferably 2 to 4 carbon atoms, most preferably acetic acid.

3. The process of claim 2 wherein said acetic acid comprises 85–95 w/v% of 20–60 w/v% aqueous glacial acetic acid with 5–15 w/v% of an organic solvent.

4. The process of claim 3 wherein said aqueous acid comprises 60 w/v% water, 30 w/v% acetic acid, and 10 w/v% tetrahydrofuran, and the reaction being carried out at a temperature between 20° to 60° C. under nitrogen.

5. The process of claims 1–4 wherein the starting compound is the (4,5,6)R, 8R-stereoisomer, or the (4,5,6)S, 8R-stereoisomer.

6. The process of claim 1 wherein said acid is a hydrogen halide, preferably hydrogen fluoride.

7. The process of claim 6 wherein said hydrolysis is effected by at least 2.05 to 10 equivalents of an aqueous solution of the acid, preferably 2.05 to 3 equivalents of hydrogen fluoride, dispersed in a water immiscible solvent, preferably a halogenated hydrocarbon, containing 2.0 to 3.0 equivalents of a mercaptan, the reaction being effected at a temperature between −30° to 50° C., preferably between 10°–50° C.

8. The process of claim 7 wherein said acid comprises 2.5 equivalents of aqueous hydrogen fluoride, the solvent is methylene chloride, the mercaptan is mercaptoethanol in an amount of 2.0 equivalents, and the reaction is effected at ambient temperature.

9. The process of claims 6–8 wherein the starting compound is the (4,5,6)R, 8R-stereoisomer, or the (4,5,6)S, 8R-stereoisomer.

10. The process of claim 1 wherein the compound of formula II or its counterpart of the unnatural prostaglandin configuration, or mixtures thereof, is made by oxidizing a compound of the formula

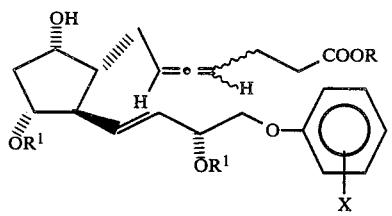

or its counterpart of the unnatural prostaglandin configuration, or mixtures thereof, wherein R, R¹, X and the wavy lines are as defined in claim 1.

11. The process of claim 10 wherein the oxidization is effected by a mild oxidant, preferably a chromium derived oxidant, most preferably chromium trioxide in the presence of 3,5-dimethylpyrazole, or Collins reagent (chromium trioxide and pyridine).

12. The process of claims 10–11 wherein the starting compound is the (4,5,6)R, 8R-stereoisomer or the (4,5,6)S, 8R-stereoisomer.

13. The process of claim 1 wherein the compound of formula II with R being a lower alkyl, or its counterpart of the unnatural prostaglandin configuration, or mixtures thereof, is formed by esterifying, preferably with a lower diazoalkane, most preferably diazomethane, the acid function of a compound of the formula

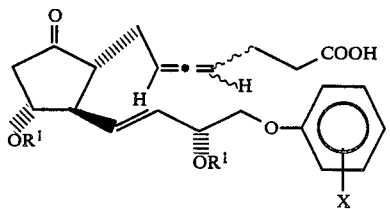

or its counterpart of the unnatural prostaglandin configuration, or mixtures thereof, wherein X, R¹ and the wavy lines are as defined in claim 1.

14. A process for preparing a compound of the formula

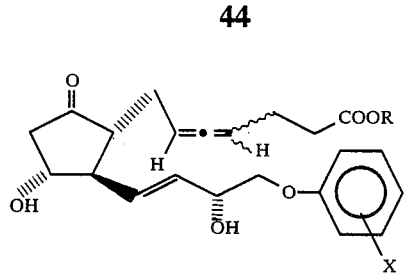

or its counterpart of the unnatural prostaglandin configuration, or mixtures thereof, with R being a lower alkyl, preferably methyl; X is hydrogen, halo, trifluoromethyl, lower alkyl or lower alkoxy, and the wavy lines represent the α or β configuration with the proviso that when one wavy line is α the other is β, which process comprises esterifying with a lower diazoalkane, preferably diazomethane, the acid of a compound of the formula

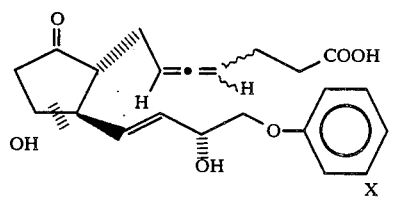

or its counterpart of the unnatural prostaglandin configuration, or mixtures thereof, wherein X and the wavy lines are as defined above.

15. A compound of the formula

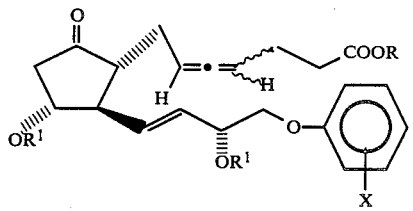

or its counterpart of the unnatural prostaglandin configuration, or mixtures thereof, wherein R is hydrogen or a lower alkyl preferably methyl; R¹ is a base-stabile acid-labile ether-forming group preferably tetrahydropyranyl, tetrahydrofuranyl or 2-ethoxyethyl, most preferably tetrahydropyranyl; X is hydrogen, halo, trifluoromethyl, lower alkyl or lower alkoxy, preferably hydrogen, and the wavy lines represent the α or β configuration with the proviso that when one wavy line is α the other is β.

16. The compound of claim 15 which is the (4,5,6)R, 8R-stereoisomer or the (4,5,6)S, 8R-stereoisomer.

17. A compound of the formula

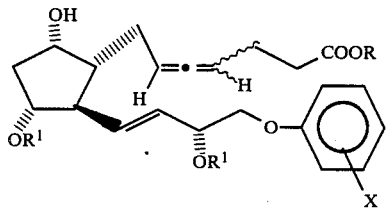

or its counterpart of the unnatural prostaglandin configuration, or mixtures thereof, wherein R is hydrogen or a lower alkyl, preferably methyl; $R^1$ is a base-stabile acid-labile ether-forming group, preferably tetrahydropyranyl, tetrahydrofuranyl or 2-ethoxyethyl, most preferably tetrahydropyranyl; X is hydrogen, halo, trifluoromethyl, lower alkyl or lower alkoxy, preferably hydrogen, and the wavy lines represent the α or β configuration with the proviso that when one wavy line is α the other is β.

18. The compound of claim 17 which is the (4,5,6)R, 8R-stereoisomer or the (4,5,6)S, 8R-stereoisomer.

19. A process for preparing a compound of the formula

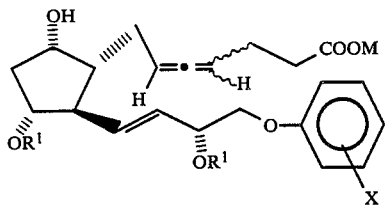

(IV)

or its counterpart of the unnatural prostaglandin configuration, or mixtures thereof, wherein M is hydrogen or an alkali metal, $R^1$ is a base-stabile acid-labile ether-forming group; X is hydrogen, halo, trifluoromethyl, lower alkyl or lower alkoxy, and the wavy lines represent the α or β configuration with the proviso that when one wavy line is α the other is β, which process comprises homologating a compound of the formula

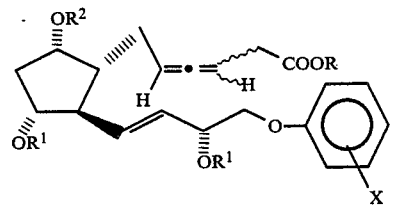

(V)

or its counterpart of the unnatural prostaglandin configuration, or mixtures thereof, wherein X, $R^1$ and the wavy lines are as defined above, $R^2$ is a base-labile ether-forming group and R is an alkyl of 1–6 carbon atoms, and optionally acidifying a compound of formula IV wherein M is an alkali metal to its corresponding free acid.

20. A process for preparing a compound of the formula

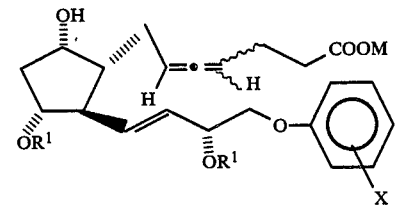

(IV)

or its counterpart of the unnatural prostaglandin configuration, or mixtures thereof, wherein M is hydrogen or an alkali metal salt, $R^1$ is a base-stabile acid-labile ether-forming group, preferably tetrahydropyranyl, tetrahydrofuranyl or 2-ethoxyethyl, most preferably tetrahydropyranyl; X is hydrogen, halo, trifluoromethyl, lower alkyl or lower alkoxy, preferably hydrogen, and the wavy lines represent the α or β configuration with the proviso that when one wavy line is α the other is β, which process comprises hydrolyzing with base preferably a strong base most preferably sodium or potassium hydroxide, a compound of the formula

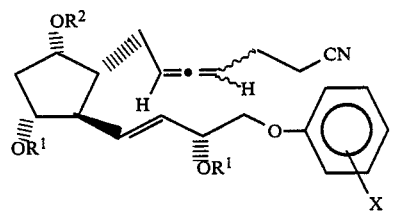

(VI)

or its counterpart of the unnatural prostaglandin configuration, or mixtures thereof, wherein $R^2$ is a base-labile ether-forming group, preferably —$SiR_4R_5R_6$ wherein $R_4$, $R_5$ and $R_6$ are the same or different and are alkyl of 1–6 carbon atoms, phenyl or arylalkyl, such as phenylalkyl, alkyl-substituted-phenylalkyl or naphthylalkyl except that all three may not be simultaneously methyl, most preferably t-butyldimethylsilyl; $R^1$, X and the wavy lines are as defined above, and optionally acidifying a compound of formula IV wherein M is an alkali metal to its corresponding free acid.

21. The process of claim 20 wherein the starting compound is the (4,5,6)R, 8R-stereoisomer or the (4,5,6)S, 8R-stereoisomer.

22. A compound of the formula

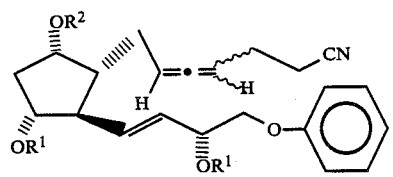

(VI)

or its counterpart of the unnatural prostaglandin configuration, or mixtures thereof, wherein $R^1$ is a base-stabile acid-labile ether-forming group, preferably tetrahydropyranyl, tetrahydrofuranyl or 2-ethoxyethyl, most preferably tetrahydropyranyl; $R^2$ is a base-labile ether-forming group, preferably —$SiR_4R_5R_6$ wherein $R_4$, $R_5$ and $R_6$ are the same or different and are alkyl of 1–6 carbon atoms, phenyl or arylalkyl, such as phenylalkyl, alkyl-substituted-phenylalkyl, or naphthylalkyl except that all three may not be simultaneously methyl, most preferably t-butyldimethylsilyl; X is hydrogen, halo, trifluoromethyl, lower alkyl or lower alkoxy, preferably hydrogen, and the wavy lines represent the α or β configuration with the proviso that when one wavy line is α the other is β.

23. The compound of claim 22 which is the (4,5,6)R, 8R-stereoisomer or the (4,5,6)S, 8R-stereoisomer.

24. A process for preparing a compound of the formula

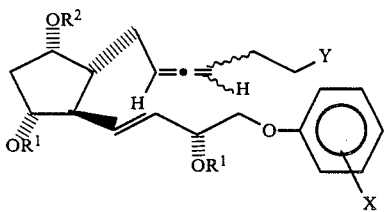
(VII)

or its counterpart of the unnatural prostaglandin configuration, or mixtures thereof, wherein $R^1$ is a base-stabile acid-labile ether-forming group, preferably tetrahydropyranyl, tetrahydrofuranyl or 2-ethoxyethyl most preferably tetrahydropyranyl; $R^2$ is a base-labile ether-forming group, preferably $-SiR_4R_5R_6$ wherein $R_4$, $R_5$ and $R_6$ are the same or different and are alkyl of 1–6 carbon atoms, phenyl or arylalkyl such as phenylalkyl alkyl-substituted-phenylalkyl or naphthylalkyl except that all three may not be simultaneously methyl, most preferably t-butyldimethylsilyl; X is hydrogen, halo, trifluoromethyl, lower alkyl or lower alkoxy preferably hydrogen and the wavy lines represent the α or β configuration with the proviso that when one wavy line is α the other is β, which process comprises reacting an alkali metal cyanide preferably sodium or potassium cyanide with a compound of the formula

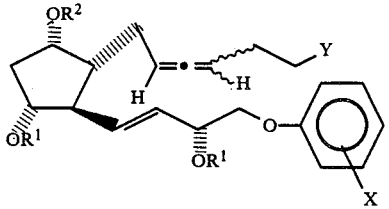
(VII)

or its counterpart of the unnatural prostaglandin configuration, or mixtures thereof, wherein Y is a halogen or $-SO_2R^3$, preferably $-SO_2R^3$ and $R^3$ is lower alkyl of 1–6 carbon atoms, aryl of 6–10 carbon atoms, aryl (6–10C) lower alkyl or substituted aryl (6–10C) lower alkyl, most preferably methyl or p-tolyl; $R^1$, $R^2$, X and the wavy lines are defined above.

25. The process of claim 24 wherein the starting compound is the (4,5,6)R, 8R-stereoisomer or the (4,5,6)S, 8R-stereoisomer.

26. A compound of the formula

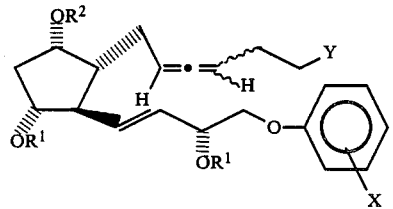
(VII)

or its counterpart of the unnatural prostaglandin configuration, or mixtures thereof, wherein Y is a leaving group such as a halogen or $-SO_2R^3$ with $R^3$ being lower alkyl of 1–6 carbon atoms, aryl of 6–10 carbon atoms, aryl (6–10C) lower alkyl or substituted aryl (6–10C) lower alkyl, preferably methanesulfonyl or p-toluenesulfonyl, $R^1$ is a base-stabile acid-labile ether-forming group, preferably tetrahydropyranyl, tetrahydrofuranyl or 2-ethoxyethyl, most preferably tetrahydropyranyl; $R^2$ is a base-labile ether-forming group, preferably $-SiR_4R_5R_6$ wherein $R_4$, $R_5$ and $R_6$ are the same or different and are alkyl of 1–6 carbon atoms, phenyl or arylalkyl such as phenylalkyl, alkyl-substituted-phenylalkyl or naphthylalkyl except that all three may not be simultaneously methyl, most preferably t-butyldimethyl; X is hydrogen, halo, trifluoromethyl, lower alkyl or lower alkoxy, preferably hydrogen, and the wavy lines represent the α or β configuration with the proviso that when one wavy line is α the other is β.

27. The compound of claim 26 which is the (4,5,6)R, 8R-stereoisomer or the (4,5,6)S, 8R-stereoisomer.

28. A process for making a compound of the formula

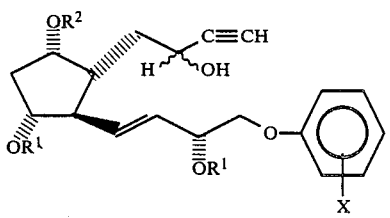
(VIII)

or its counterpart of the unnatural prostaglandin configuration, or mixtures thereof, wherein R is lower alkyl; $R^1$ is a base-stabile, acid labile ether forming group, preferably tetrahydropyranyl, tetrahydrofuranyl or 2-ethoxyethyl, most preferably tetrahydropyranyl; $R^2$ is a base-labile ether forming group, preferably $-SiR_4R_5R_6$ wherein $R_4$, $R_5$ and $R_6$ are the same or different and are alkyl of 1–6 carbon atoms, phenyl or arylalkyl such as phenylalkyl, alkyl-substituted-phenylalkyl or naphthylalkyl except that all three may not be simultaneously methyl, most preferably t-butyldimethylsilyl; X is hydrogen, halo, trifluoromethyl, lower alkyl or lower alkoxy, preferably hydrogen, and the wavy lines represent the α or β configuration with the proviso that when one wavy line is α the other is β, which process comprises reacting a propargyl alcohol of the following formula

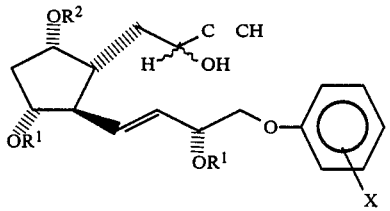
(VIII)

or its counterpart of the unnatural prostaglandin configuration, or mixtures thereof, wherein $R^1$, $R^2$, X and the wavy lines are defined above, with a lower alkyl orthoacetate and a catalytic amount of a lower alkanoic acid.

29. The process of claim 28 wherein the trialkyl orthoacetate is triethyl orthoacetate and the alkanoic acid of 1–6 carbon atoms, preferably acetic acid or propionic acid in a quantity of 0.1–5% by volume relative to the volume of triethyl orthoacetate and the process is carried out at an elevated temperature preferably at a temperature of between 100°–130° C.

30. A compound of the formula

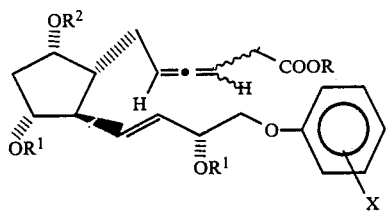

or its counterpart of the unnatural prostaglandin configuration, or mixtures thereof, wherein R is lower alkyl; $R^1$ is a base-stabile ether forming group preferably tetrahydropyranyl, tetrahydrofuranyl or 2-ethoxyethyl, most preferably tetrahydropyranyl; $R^2$ is a base-labile ether forming group, preferably $-SiR_4R_5R_6$ wherein $R_4$, $R_5$ and $R_6$ are the same or different and are alkyl of 1-6 carbon atoms, phenyl or arylalkyl such as phenylalkyl, alkyl-substituted-phenylalkyl or naphthylalkyl except that all three may not be simultaneously methyl, most preferably t-butyldimethylsilyl; X is hydrogen, halo, trifluoromethyl, lower alkyl or lower alkoxy, preferably hydrogen, and the wavy lines represent the α or β configuration with the proviso that when one wavy line is α the other is β.

31. The compound of claim 30 which is the (4,5,6)R, 8R-stereoisomer or the (4,5,6)S, 8R-stereoisomer.

32. A compound of the formula

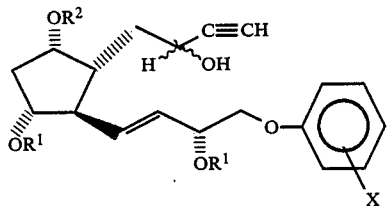

or its counterpart of the unnatural prostaglandin configuration, or mixtures thereof, wherein $R^1$ is a base-stabile ether-forming group, preferably tetrahydropyranyl, tetrafuranyl or 2-ethoxyethyl, most preferably tetrahydropyranyl; $R^2$ is a base-labile ether-forming group, preferably $-SiR_4R_5R_6$ wherein $R_4$, $R_5$ and $R_6$ are the same or different and are alkyl of 1-6 carbon atoms, phenyl or arylalkyl such as phenylalkyl, alkyl-substituted-phenylalkyl or naphthylalkyl except that all three may not be simultaneously methyl, most preferably t-butyldimethylsilyl; X is hydrogen, halo, trifluoromethyl, lower alkyl or lower alkoxy, preferably hydrogen, and the wavy lines represent the α or β configuration with the proviso that when one wavy line is α the other is β.

33. The compound of claim 32 which is the 6R, 8R-stereoisomer or the 6S, 8R-stereoisomer.

34. A process for preparing a compound of the formula

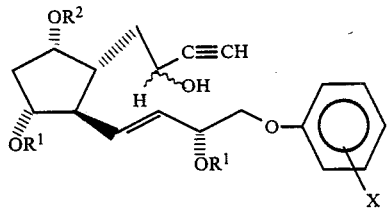

or its counterpart of the unnatural prostaglandin configuration, or mixtures thereof, wherein $R^1$ is a base-stabile, acid-labile ether-forming group; $R^2$ is a base-labile ether-forming group; X is hydrogen, halo, trifluoromethyl, lower alkyl or lower alkoxy, and the wavy lines represent the α or β configuration with the proviso that when one wavy line is α the other is β, which process comprises treating with a metal acetylide in an inert solvent a compound of the formula

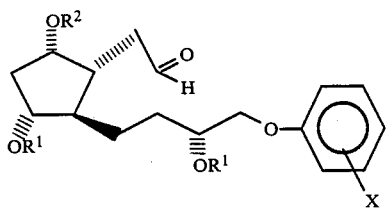

or a racemic or non-racemic mixture thereof, wherein $R^1$, $R^2$ and X are defined above, and optionally separating the diastereomers of formula VIII by chromatography.

35. The process of claim 34 wherein the metal acetylide is ethynyl magnesium chloride, ethynyl magnesium bromide, ethynyl magnesium iodide, ethynyl lithium or lithium acetylide ethylene diamine complex, the reaction being carried out in a halogenated lower alkane, preferably methylene chloride, an ether or toluene at a temperature between 0°-50° C., preferably 20°-30° C.

36. A compound of the formula

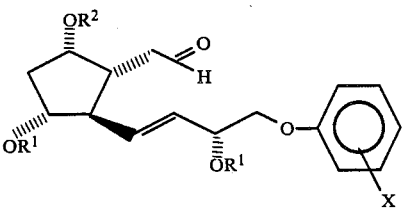

or a racemic or non-racemic mixture thereof wherein $R^1$ is or a base-stabile, acid-labile ether-forming group, preferably tetrahydropyranyl, tetrahydrofuranyl or 2-ethoxyethyl, most preferably tetrahydropyranyl; $R^2$ is a base-labile ether-forming group, preferably $-SiR_4R_5R_6$ wherein $R_4$, $R_5$ and $R_6$ are the same or different and are alkyl of 1-6 carbon atoms, phenyl or arylalkyl such as phenylalkyl, alkyl-substituted-phenylalkyl or naphthylalkyl except that all three may not be simultaneously methyl, most preferably t-butyldimethylsilyl; and X is hydrogen, halo, trifluoromethyl, lower alkyl or lower alkoxy, preferably hydrogen.

37. A process for preparing a compound of the formula

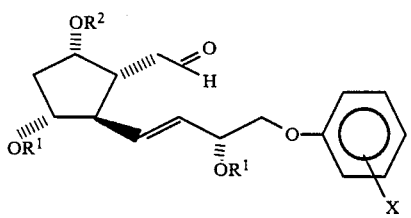

(IX)

or a racemic or non-racemic mixture thereof wherein $R^1$ is a base-stabile, acid-labile ether-forming group, preferably tetrahydropyranyl, tetrahydrofuranyl or 2-ethoxyethyl, most preferably tetrahydropyranyl; $R^2$ is a base-labile ether-forming group, preferably —$SiR_4R_5R_6$ wherein $R_4$, $R_5$ and $R_6$ are the same or different and are alkyl of 1–6 carbon atoms, phenyl or arylalkyl such as naphthylalkyl except that all three may not be simultaneously methyl, most preferably t-butyldimethylsilyl; X is hydrogen, halo, trifluoromethyl, lower alkyl or lower alkoxy, preferably hydrogen, which process comprises oxidizing with a chromium-based mild oxidant a compound of the formula

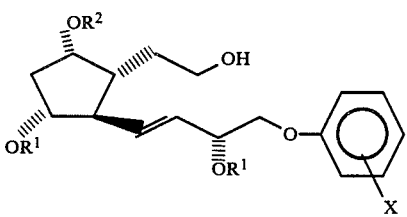

(X)

or a racemic or non-racemic mixture thereof, wherein $R^1$, $R^2$ and X are defined above.

38. The process of claim 37 wherein the oxidant is chromium trioxide in the presence of 3,5-dimethylpyrazole or Collins reagent (chromium trioxide and pyridine).

39. A process for preparing a compound of the formula

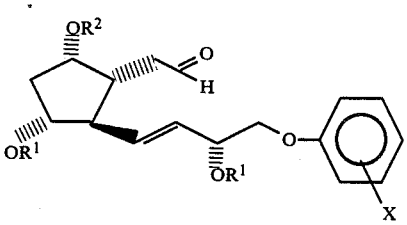

(IX)

or a racemic or non-racemic mixture thereof wherein $R^1$ is a base-stabile, acid-labile ether-forming group, preferably tetrahydropyranyl, tetrahydrofuranyl or 2-ethoxyethyl, most preferably tetrahydropyranyl; $R^2$ is a base-labile ether-forming group, preferably —$SiR_4R_5R_6$ wherein $R_4$, $R_5$ and $R_6$ are the same or different and are alkyl of 1–6 carbon atoms, phenyl or arylalkyl such as naphthylalkyl except that all three may not be simultaneously methyl, most preferably t-butyldimethylsilyl; X is hydrogen, halo, trifluoromethyl, lower alkyl or lower alkoxy, preferably hydrogen, which process comprises reducing a compound of the formula

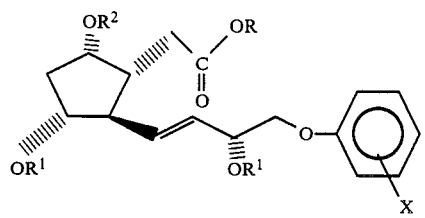

(XI)

or a racemic or non-racemic mixture thereof, wherein X, $R^1$, $R^2$ are as described above and R is alkyl of 1–6 carbon atoms.

40. The process of claim 39 wherein the reduction is carried out by a reducing agent such as diisobutylaluminum hydride at low temperature.

41. A process for preparing a compound of the formula

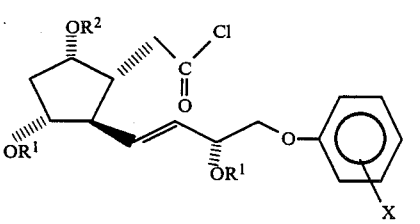

(IX)

or a racemic or non-racemic mixture thereof wherein $R^1$ is a base-stabile, acid-labile ether-forming group, preferably tetrahydropyranyl, tetrahydrofuranyl or 2-ethoxyethyl, most preferably tetrahydropyranyl; $R^2$ is a base-labile ether-forming group, preferably —$SiR_4R_5R_6$ wherein $R_4$, $R_5$ and $R_6$ are the same or different and are alkyl of 1–6 carbon atoms, phenyl or arylalkyl such as naphthylalkyl except that all three may not be simultaneously methyl, most preferably t-butyldimethylsilyl; X is hydrogen, halo, trifluoromethyl, lower alkyl or lower alkoxy, preferably hydrogen, which process comprises reducing a compound of the formula

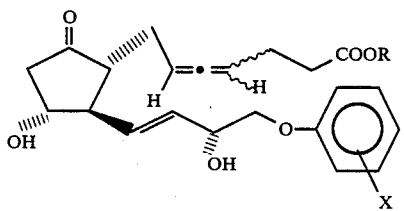

(XII)

or a racemic or non-racemic mixture thereof, wherein $R^1$, $R^2$ and X are as defined above with hydrogen and palladium on barium sulfate.

42. A process for preparing a compound of the formula or its counterpart of the unnatural prostaglandin configuration, or mixtures thereof, wherein R is hydrogen or lower alkyl, preferably methyl; X is hydrogen, halo, trifluoromethyl, lower alkyl or lower alkoxy, preferably hydrogen, and the wavy lines represent the α or β configuration with the proviso that when one wavy line is α the other is β or a pharmaceutically acceptable, non-toxic salt of the compound of formula I wherein R is hydrogen, which process comprises:

(a) reacting a propargyl alcohol of the formula

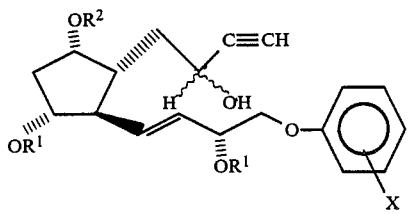
(VIII)

or its counterpart of the unnatural prostaglandin configuration, or mixtures thereof, wherein X and the wavy lines are as defined above, $R^1$ is a base-stabile, acid-labile ether-forming group and $R^2$ is a base-labile ether-forming group with a lower trialkyl orthoacetate and a catalytic amount of a lower alkanoic acid to obtain a compound of the formula

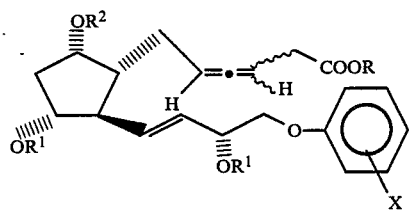
(V)

or its counterpart of the unnatural prostaglandin configuration, or mixtures thereof, wherein X, $R^1$, $R^2$ and the wavy lines are as defined above and R is an alkyl of 1-6 carbon atoms; and (b) homologating the ester obtained in step (a) and hydrolyzing the base-labile ether-forming —$OR^2$ group to obtain a compound of the formula

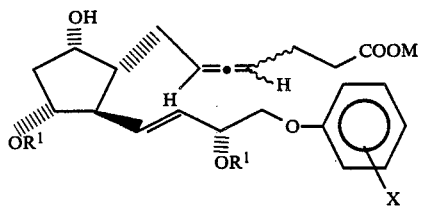
(IV)

or its counterpart of the unnatural prostaglandin configuration, or mixtures thereof, where X, $R^1$ and the wavy lines are as defined above, M is an alkali metal; and (c) acidifying the salt obtained in step (b) to obtain the corresponding free acid, and optionally (d) esterifying the acid obtained in step (c) to obtain a compound of the formula

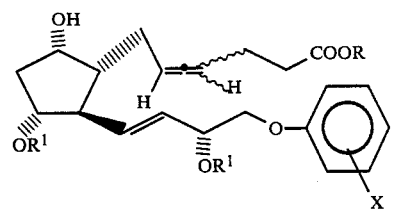
(III)

or its counterpart of the unnatural prostaglandin configuration, or mixtures thereof, wherein X, $R^1$ and wavy lines are as defined above, R is an alkyl of 1-6 carbon atoms, and (e) oxidizing the acid obtained in step (c) or the ester obtained in step (d) to obtain a compound of the formula

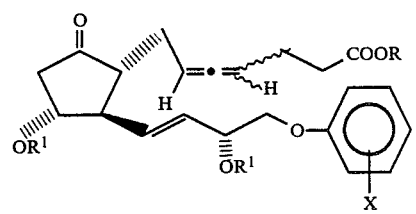
(II)

or its counterpart of the unnatural prostaglandin configuration, or mixtures thereof, wherein X, $R^1$ and the wavy lines are as defined above, R is hydrogen or an alkyl or 1-6 carbon atoms; and (f) hydrolyzing the protecting group $R^1$ in the compound obtained in step (e) with an acid to obtain a compound of the formula

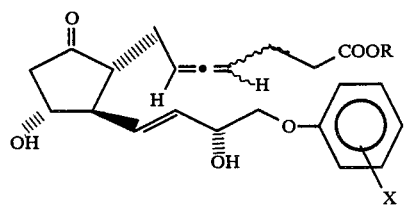
(I)

or its counterpart of the unnatural prostaglandin configuration, or mixtures thereof, wherein X, R and the wavy lines are as defined above, and optionally (g) esterifying a compound obtained in step (f) wherein R is hydrogen to the corresponding compound wherein R is an alkyl of 1-6 carbon atoms, and optionally (h) converting a compound of formula I wherein R is hydrogen to its corresponding pharmaceutically acceptable, non-toxic salts.

43. The process of claim 42 wherein the homologation step (b) is carried out by (a) reducing a compound of the formula

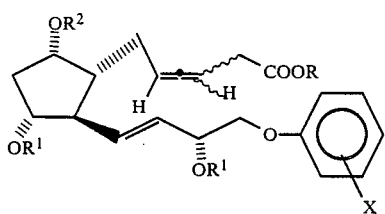 (V)

or its counterpart of the unnatural prostaglandin configuration, or mixtures thereof, wherein R, $R^1$, $R^2$, X and the wavy lines are as defined in step (a) of claim 42, to a primary alcohol of the formula

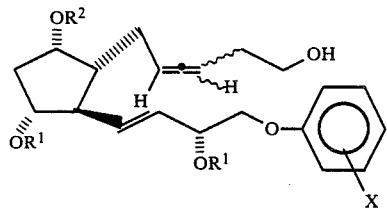

or its counterpart of the unnatural prostaglandin configuration, or mixtures thereof, wherein X, $R^1$, $R^2$ and the wavy lines are as defined above, and (b) converting the alcohol obtained in preceding step (a) to a compound of the formula

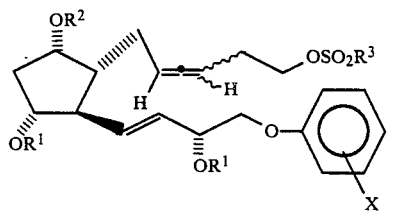 (VII)

or its counterpart of the unnatural prostaglandin configuration, or mixtures thereof, wherein X, $R^1$, $R^2$ and the wavy lines are as defined above and $R^3$ is lower alkyl of 1-6 carbon atoms, aryl of 6-10 carbon atoms, aryl (6-10C) lower alkyl or substituted aryl (6-10C) lower alkyl, and (c) reacting the compound or mixture obtained in preceding step (b) with an alkali metal cyanide to obtain a compound of the formula

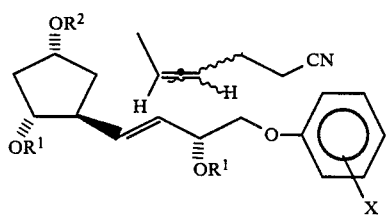 (VI)

or its counterpart of the unnatural prostaglandin configuration, or mixtures thereof, wherein X, $R^1$, $R^2$ and the wavy lines are as defined above, and (d) hydrolyzing the compound obtained in preceding step (c) with a strong base to obtain a compound of the formula

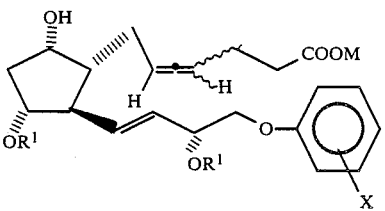 (IV)

or its counterpart of the unnatural prostaglandin configuration, or mixtures thereof, wherein X, $R^1$ and the wavy lines are as defined above and M is an alkali metal.

44. The process of claim 43 wherein the reduction step (a) is carried out by using a metal hydride, such as lithium aluminum hydride or diisobutylaluminum hydride in an aprotic polar solvent, preferably under an inert atmosphere at the reflux temperature of the solvent.

45. The process of claim 43 wherein the conversion step (b) is carried out by reacting said alcohol with an lower alkyl or aryl sulfonate ester, such as methanesulfonyl chloride or p-toluenesulfonyl chloride, in an organic solvent at a temperature between $-40°$ and $25°$ C.

46. The process of claim 43 wherein in step (c) said sulfonate ester is reacted with sodium or potassium cyanide in a polar solvent at a temperature between $50°-120°$ C.

47. The process of claim 43 wherein in the hydrolysis step (d) the strong base is an alkali metal hydroxide preferably lithium, sodium or potassium hydroxide.

48. The process of claim 42 wherein the oxidation step (e) is carried out by using a mild oxidizing agent preferably chromium trioxide in the presence of 3,5-dimethylpyrazole or Collins reagent in a polar solvent.

49. The process of claim 42 wherein the hydrolysis step (f) is carried out by an alkanoic acid of 1-6 carbon atoms, preferably acetic acid or a hydrogen halide, preferably hydrogen fluoride.

50. Methyl (4,5,6R,8R)-9-oxo-11a,15a-dihydroxy-16-phenoxy-17,18,19,20-tetranorprosta-4,5,13(E)-trienoate of the following formula

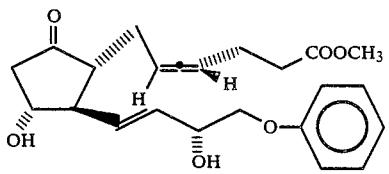

51. The compound of claim 50 in crystalline form.

52. A process for preparing crystalline compound of claim 51, which process comprises cooling an oily material of the compound of claim 50 to a lower temperature preferably at a temperature between $-20°$ to $0°$ C.

53. A pharmaceutical composition for the treatment or prevention of gastric or duodenal ulcers which comprises a therapeutically effective amount of the compound of claims 50 or 51 in admixture with one or more pharmaceutically acceptable excipients.

54. A method for treating gastric or duodenal ulcers which method comprises administering to a mammal a therapeutically effective amount of the compound of claims 50 or 51.

55. The compound of claims 50 or 51 prepared according to claim 1-14 or 42-49.

56. The use of the compound of claims 50 or 51 in the preparation of a pharmaceutical composition.

57. A process according to claims 1-14 or 42-49 wherein the active ingredient of claims 50 or 51 prepared in accordance with claims 1-14 or 42-49 is mixed with a pharmaceutically acceptable carrier.

* * * * *

UNITED STATES PATENT AND TRADEMARK OFFICE
CERTIFICATE OF CORRECTION

PATENT NO. : 4,780,562
DATED : October 25, 1988
INVENTOR(S) : GARY F. COOPER et al.

It is certified that error appears in the above-identified patent and that said Letters Patent is hereby corrected as shown below:

On the cover page, "Date of Patent" section, an asterisk should be inserted to the left of "October 25, 1988"; below the "Assignee" section should be inserted
--[*] Notice: The portion of the term of this patent subsequent to July 15, 2003 has been disclaimed. --

Claims 1-49 and 55-57 should be deleted.

Claims 50-54 should be renumbered as Claims 1-5, respectively.

In Claim 1 (previously Claim 50), lines 1-2, "Methyl (4,5,6R,8R)-9-oxo-11a,15a-dihydroxy-16-phenoxy-17,18,19,20-tetranorprosta-4,5,13(E)-trienoate" should read -- Methyl (4,5,6R,8R)-9-oxo-11$\alpha$,15$\alpha$-dihydroxy-16-phenoxy-17,18,19,20-tetranorprosta-4,5,13(E)-trienoate --.

Title page, "57 Claims, No Drawings" should read --5 Claims, No Drawings--.

Signed and Sealed this

Twenty-fifth Day of July, 1989

*Attest:*

DONALD J. QUIGG

*Attesting Officer*  *Commissioner of Patents and Trademarks*